US012611548B2

(12) United States Patent
Segal et al.

(10) Patent No.: US 12,611,548 B2
(45) Date of Patent: Apr. 28, 2026

(54) TREATMENT APPARATUS, SYSTEMS AND METHODS

(71) Applicant: BRAINQ TECHNOLOGIES LTD., Jerusalem (IL)

(72) Inventors: Yaron Segal, Jerusalem (IL); Yael Djemal-Kay, Jerusalem (IL)

(73) Assignee: BrainQ Technologies Ltd., Jerusalem (IL)

( * ) Notice: Subject to any disclaimer, the term of this patent is extended or adjusted under 35 U.S.C. 154(b) by 966 days.

(21) Appl. No.: 17/771,566

(22) PCT Filed: Nov. 18, 2020

(86) PCT No.: PCT/IL2020/051193
§ 371 (c)(1),
(2) Date: Apr. 25, 2022

(87) PCT Pub. No.: WO2021/117029
PCT Pub. Date: Jun. 17, 2021

(65) Prior Publication Data
US 2022/0379133 A1     Dec. 1, 2022

Related U.S. Application Data

(60) Provisional application No. 63/071,599, filed on Aug. 28, 2020, provisional application No. 62/946,754, filed on Dec. 11, 2019.

(51) Int. Cl.
*A61N 2/02*        (2006.01)
*A61N 2/00*        (2006.01)
(52) U.S. Cl.
CPC ............... *A61N 2/02* (2013.01); *A61N 2/006* (2013.01)

(58) Field of Classification Search
CPC .......... A61N 2/00; A61N 2/002; A61N 2/004; A61N 2/006; A61N 2/008; A61N 2/02
See application file for complete search history.

(56) References Cited

U.S. PATENT DOCUMENTS

| | | | | |
|---|---|---|---|---|
| 5,195,941 A | * | 3/1993 | Erickson .................. | A61N 2/02 600/15 |
| 5,314,401 A | * | 5/1994 | Tepper ..................... | A61N 2/02 600/15 |

(Continued)

FOREIGN PATENT DOCUMENTS

| | | |
|---|---|---|
| CN | 1457905 | 11/2003 |
| CN | 1879906 | 12/2006 |

(Continued)

OTHER PUBLICATIONS

Notice of Reason(s) for Rejection Dated Jul. 23, 2024 From the Japan Patent Office Re. Application No. 2022-524662 and Its Translation Into English. (9 Pages).

(Continued)

*Primary Examiner* — Carrie R Dorna

(57)        ABSTRACT

Body wearable treatment apparatus for treatment of neurological disorders and conditions of the central nervous system by application of electromagnetic fields thereto, the apparatus including a coil mounting portion and a body mounting portion, the coil mounting portion being removably mounted on the body mounting portion and a system including at least one database storing information relating to treatment protocols, a server communicating with the at least one database and body wearable treatment apparatus communicating with the server, the body wearable treatment apparatus including a coil mounting portion and a body mounting portion, the coil mounting portion being removably mounted on the body mounting portion.

21 Claims, 18 Drawing Sheets

(56) References Cited

U.S. PATENT DOCUMENTS

| | | | | |
|---|---|---|---|---|
| 5,478,303 | A * | 12/1995 | Foley-Nolan | A61N 1/40 600/15 |
| 6,024,691 | A * | 2/2000 | Tepper | A61N 2/02 600/15 |
| 6,443,883 | B1 | 9/2002 | Ostrow et al. | |
| 6,463,328 | B1 | 10/2002 | John | |
| 9,392,956 | B2 | 7/2016 | Luo et al. | |
| 9,694,197 | B2 | 7/2017 | Segal | |
| 10,322,295 | B2 | 6/2019 | Segal | |
| 2004/0002635 | A1 | 1/2004 | Hargrove et al. | |
| 2005/0182287 | A1 | 8/2005 | Becker | |
| 2006/0122496 | A1 | 6/2006 | George et al. | |
| 2006/0129022 | A1 * | 6/2006 | Venza | A61N 2/008 600/13 |
| 2008/0139871 | A1 | 6/2008 | Muntermann | |
| 2009/0099627 | A1 | 4/2009 | Molnar et al. | |
| 2009/0306491 | A1 | 12/2009 | Haggers | |
| 2010/0016651 | A1 | 1/2010 | Sivo | |
| 2010/0210894 | A1 | 8/2010 | Pascual-leone et al. | |
| 2011/0046432 | A1 | 2/2011 | Simon et al. | |
| 2011/0112427 | A1 | 5/2011 | Phillips et al. | |
| 2011/0190849 | A1 | 8/2011 | Faltys et al. | |
| 2011/0295350 | A1 | 12/2011 | Mercanzini et al. | |
| 2012/0238835 | A1 | 9/2012 | Hyde et al. | |
| 2012/0271375 | A1 | 10/2012 | Wu et al. | |
| 2013/0268016 | A1 | 10/2013 | Xi et al. | |
| 2014/0023999 | A1 | 1/2014 | Greder | |
| 2014/0148657 | A1 | 5/2014 | Hendler et al. | |
| 2014/0163304 | A1 | 6/2014 | Burnett et al. | |
| 2014/0179986 | A1 | 6/2014 | Kelley | |
| 2014/0200388 | A1 | 7/2014 | Schneider et al. | |
| 2014/0303425 | A1 | 10/2014 | Pilla et al. | |
| 2015/0018706 | A1 | 1/2015 | Segal | |
| 2015/0066104 | A1 | 3/2015 | Wingeier et al. | |
| 2015/0105837 | A1 | 4/2015 | Aguilar Domingo | |
| 2015/0112409 | A1 | 4/2015 | Hagedorn | |
| 2015/0133718 | A1 | 5/2015 | Schneider et al. | |
| 2015/0257700 | A1 | 9/2015 | Fu | |
| 2015/0375005 | A1 | 12/2015 | Segal | |
| 2016/0015995 | A1 * | 1/2016 | Leung | A61N 2/008 600/14 |
| 2016/0136427 | A1 | 5/2016 | De Ridder | |
| 2016/0184599 | A1 | 6/2016 | Segal | |
| 2016/0213276 | A1 | 7/2016 | Gadot et al. | |
| 2016/0220836 | A1 | 8/2016 | Parks | |
| 2017/0165485 | A1 * | 6/2017 | Sullivan | A61B 5/0022 |
| 2017/0296837 | A1 | 10/2017 | Jin | |
| 2018/0043174 | A1 | 2/2018 | Gurfein | |
| 2018/0050216 | A9 | 2/2018 | Burnett | |
| 2018/0064950 | A1 | 3/2018 | Segal | |
| 2018/0214710 | A1 | 8/2018 | Charles et al. | |
| 2019/0209856 | A1 | 7/2019 | Segal | |
| 2019/0290925 | A1 * | 9/2019 | Gellman | A61N 2/004 |
| 2019/0358465 | A1 | 11/2019 | Segal | |
| 2020/0001041 | A1 * | 1/2020 | Kranck | A61M 21/02 |
| 2023/0372725 | A1 | 11/2023 | Segal | |

FOREIGN PATENT DOCUMENTS

| | | | | |
|---|---|---|---|---|
| CN | 103917156 | | 7/2014 | |
| CN | 104902806 | A | 9/2015 | |
| CN | 107041750 | | 8/2017 | |
| CN | 109906103 | | 6/2019 | |
| CN | 110141780 | | 8/2019 | |
| CN | 209253537 | | 8/2019 | |
| DE | 202010005501 | * | 8/2010 | A61N 2/02 |
| EP | 2755550 | | 6/2019 | |
| JP | 2007-520290 | | 7/2007 | |
| JP | 2014-501582 | | 1/2014 | |
| JP | 2014-526336 | | 10/2014 | |
| KR | 10-2016-0007729 | | 1/2016 | |
| WO | WO 2004078260 | * | 9/2004 | A61N 2/02 |
| WO | 2011/057028 | | 5/2011 | |
| WO | 2013/038400 | | 3/2013 | |
| WO | 2015/022679 | | 2/2015 | |
| WO | 2015/187712 | | 12/2015 | |
| WO | 2016/046830 | | 3/2016 | |
| WO | 2018/047164 | | 3/2018 | |
| WO | WO 2019/161407 | | 8/2019 | |
| WO | 2021/117029 | | 6/2021 | |

OTHER PUBLICATIONS

Notice of Allowance dated Sep. 27, 2022, which issued during the prosecution of U.S. Appl. No. 16/441,614.
Notice of Allowance dated Oct. 21, 2022, which issued during the prosecution of Australian Patent Application No. 2017323663.
An Office Action together with an English Summary dated Aug. 29, 2022 which issued during the prosecution of Korean Patent Application No. 10-2019-7009744.
An Office Action together with an English Summary dated Oct. 17, 2022 which issued during the prosecution of Chinese Patent Application No. 10-2019-201780068350.3.
Notice of Allowance Dated Apr. 7, 2023 from the US Patent and Trademark Office Re. U.S. Appl. No. 16/330,670. (7 pages).
Communication Pursuant to Article 94(3) EPC Dated Sep. 11, 2023 From the European Patent Office Re. Application No. 17848278.2. (4 Pages).
Supplementary European Search Report and the European Search Opinion Dated Apr. 3, 2023 From the European Patent Office Re. Application No. 20899302.2. (7 Pages).
U.S. Appl. No. 62/642,037, filed Mar. 13, 2018.
Xiong, Ye, Asim Mahmood, and Michael Chopp. "Neurorestorative treatments for .traumatic brain injury." Discovery medicine 10.54 (2010): 434.
An International Search Report and a Written Opinion both dated Dec. 20, 2017, which issued during the prosecution of Applicant's PCT/IL2017/050981.
U.S. Appl. No. 62/946,762, filed Dec. 11, 2019.
U.S. Appl. No. 62/946,754, filed Dec. 11, 2019.
An English translation of an Office Action dated Jan. 27, 2016 which issued during the prosecution of Chinese Patent Application No. 201280055647.3.
Niehaus, L., et al. "Abnormal postexcitatory and interhemispheric motor cortex .inhibition in writer's cramp." Journal of neurology 248.1 (2001): 51-52.
Rosenbaum, R. Shayna, et al. "The case of KC: contributions of a memory-.impaired person to memory theory." Neuropsychologia 43.7 (2005): 989-1021.
Emery, Gregory, et al. "Asymmetric Rab11 endosomes regulate delta recycling and specify cell fate in the Drisophila nervous system." Cell 122.5 (2005): 763-.773.
Khanna, Michael J. "The cognitive correlates of human brain oscillations." Journal .of Neuroscience 26.6 (2006): 1669-1672.
Kernie, Steven G., Trent M. Erwin, and Luis F. Parada. "Brain remodeling due to neuronal and astrocytic proliferation after controlled cortical injury in mice." .Journal of neuroscience research 66.3 (2001): 317-326.
U.S. Appl. No. 62/642,038, filed Mar. 13, 2018.
U.S. Appl. No. 61/533,917, filed Sep. 13, 2011.
European Search Report dated Mar. 17. 2015, which issued during the prosecution of Applicant's European App No. 12831890.4.
An International Search Report and a Written Opinion both dated Oct. 22. 2012, which issued during the prosecution of Applicant's PCT/IL2012/000255.
An International Preliminary Report on Patentability dated Mar. 12, 2019, which issued during the prosecution of Applicant's PCT/IL2017/050981.
An English translation of an Office Action dated May 28, 2015 which issued during the prosecution of Chinese Patent Application No. 201280055647.3.
U.S. Appl. No. 62/747,671, filed Oct. 19, 2018.
An English translation of an Office Action dated May 31, 2016, which issued during the prosecution of Japanese Patent Application No. 2014-530377.

(56) References Cited

OTHER PUBLICATIONS

An English translation of an Office Action dated Mar. 7, 2017, which issued during the prosecution of Japanese Patent Application No. 2014-530377.

An Office Action dated Jun. 1. 2016, which issued during the prosecution of U.S. Appl. No. 14/344,606.

An Office Action dated Oct. 24, 2016, which issued during the prosecution of U.S. Appl. No. 14/344,606.

Nithianandasivam, Nartani. "Oligodendrocytes, Myelin and Multiple Sclerosis." .(2018) University of Toronto Medical Journal 95.1.

An Office Action dated Jun. 29, 2018, which issued during the prosecution of U.S. Appl. No. 15/257,900.

Notice of Allowance dated Apr. 10, 2019, which issued during the prosecution of U.S. Appl. No. 15/257,900.

Notice of Allowance dated Feb. 28, 2019, which issued during the prosecution of U.S. Appl. No. 15/257,900.

Notice of Allowance dated Mar. 20, 2017, which issued during the prosecution of U.S. Appl. No. 14/344,606.

Notice of Allowance dated Apr. 5, 2017, which issued during the prosecution of Australian Patent Application No. 2012310074.

An Office Action dated Apr. 15, 2016, which issued during the prosecution of Australian Patent Application No. 2012310074.

An Office Action dated Mar. 28, 2018, which issued during the prosecution of Canadian Patent Application No. 2,848,549.

An English Translation of an Office Action dated Oct. 19, 2017, which issued during the prosecution of Israel Patent Application No. 231486. (the relevant part only).

Mantovani, Lorenzo Giovanni, et al. "Tecfidera® (delayed-release dimethylfumarate) in the treatment of relapsing-remitting multiple sclerosis." Farmeconomia. Health economics and therapeutic pathways 18.2S (2017).

Maynard, Frederick M., et al. "International standards for neurological and functional classification of spinal cord injury." Spinal cord 35.5 (1997): 266-274.

European Search Report dated Mar. 13, 2020, which issued during the prosecution of Applicant's European App No. 17848278.2.

An Office Action dated Feb. 17. 2020, which issued during the prosecution of Indian Patent Application No. 2133/DELNP/2014.

Elhalel, G., et al. "Cardioprotection from stress conditions by weak magnetic fields .in the Schumann Resonance band." Scientific reports 9.1 (2019): 1-10.

Lee, Hae Ung, et al. "Subcellular electrical stimulation of neurons enhances the .myelination of axons by oligodendrocytes." PloS one 12.7 (2017): e0179642.

An International Search Report and a Written Opinion both dated Mar. 26, 2021, which issued during the prosecution of Applicant's PCT/IL2020/051193.

An Office Action dated Dec. 4, 2020 which issued during the prosecution of Applicant's European App No. 17848278.2.

Cichon, Natalia, et al. "Increase in blood levels of growth factors involved in the neuroplasticity process by using an extremely low frequency electromagnetic field in post-stroke patients." Frontiers in Aging Neuroscience 10 (2018): 294.

Cichoń, Natalia, et al. "Benign effect of extremely low-frequency electromagnetic field on brain plasticity assessed by nitric oxide metabolism during poststroke rehabilitation." Oxidative Medicine and Cellular Longevity 2017 (2017).

Ramos-Cejudo, Jaime, et al. "Traumatic brain injury and Alzheimer's disease: the .cerebrovascular link." EBioMedicine 28 (2018): 21-30.

Ross, Christina L., and Benjamin S. Harrison. "Effect of pulsed electromagnetic field on inflammatory pathway markers in RAW 264.7 murine macrophages." .Journal of inflammation research 6 (2013): 45.

Shih, Yao-Hsiang, et al. "Hypertension accelerates Alzheimer's disease-related .pathologies in pigs and 3xTg mice." Frontiers in aging neuroscience 10 (2018): 73.

Sorensen, Per Soelberg, and Morten Blinkenberg. "The potential role for ocrelizumab in the treatment of multiple sclerosis: current evidence and future .prospects." Therapeutic advances in neurological disorders 9.1 (2016): 44-52.

Zeilig, G., Gaidukov, E., Tavor, I., Livny, A., Alter, A., & Segal, Y. (2018). A Beneficial Effect Of A Brain Computer Interface Based Stimulation Device Aimed At Spinal Cord Injury Patients Impaired Neural Networks Improving surf water safety in Mediterranean Region View project acoustic Signal analysis View project Beneficial EFFE. Retrieved from https://www.researchgate.net/publication/323108758.

Wang, Shiqian, et al. "Design and control of the MINDWALKER exoskeleton." IEEE transactions on neural systems and rehabilitation engineering 23.2 (2014): .277-286.

Yakir-Blumkin, M. Ben, et al. "Neuroprotective Effect of Weak Static Magnetic Fields in Primary Neuronal Cultures." .Neuroscience 278 (2014): 313-326.

An Office Action dated Aug. 17, 2021, which issued during the prosecution of U.S. Appl. No. 16/330,670.

Fotiou, D. F., et al. "Cholinergic deficiency in Alzheimer's and Parkinson's disease: Evaluation with pupillometry." International Journal of Psychophysiology .73 (2009): 143-149.

Gamito, Pedro, et al. "Cognitive training on stroke patients via virtual reality-based .serious games." Disability and rehabilitation 39.4 (2017): 385-388.

Westerberg, H., et al. "Computerized working memory training after stroke—.A pilot study." Brain Injury 21.1 (2007): 21-29.

Gravanis, Iordanis, and Stella E. Tsirka. "tPA as a therapeutic target in stroke." .(2008) Expert opinion on therapeutic targets 12.2.

Kirshblum, Steven C., et al. "International standards for neurological classification of spinal cord injury (Revised 2011)." The Journal of Spinal Cord Medicine 34.6 .(2011): 535.

An Office Action dated Feb. 3, 2022, which issued during the prosecution of U.S. Appl. No. 16/330,670.

An Office Action dated Mar. 25, 2022, which issued during the prosecution of U.S. Appl. No. 16/330,670.

An English translation of an Office Action dated Jul. 6, 2021, which issued during the prosecution of Japanese Patent Application No. 2019-533724.

An English translation of an Office Action dated Mar. 29, 2022, which issued during the prosecution of Japanese Patent Application No. 2019-533724.

An Office Action dated Mar. 29, 2022, which issued during the prosecution of U.S. Appl. No. 16/441,614.

Malone, Misti, et al. "Neuronal activity promotes myelination via a cAMP .pathway." Glia 61.6 (2013): 843-854—Abstract.

Hojati, Zohreh, Maryam Kay, and Fariba Dehghanian. "Mechanism of action of interferon beta in treatment of multiple sclerosis." Multiple sclerosis. Academic Press, 2016. 365-392—Abstract accessed on Aug. 28, 2022 {.https://www.sciencedirect.com/science/article/pii/B9780128007631000154}.

Johnson, Jon W., and Shawn E. Kotermanski. "Mechanism of action of memantine." Current opinion in pharmacology 6.1 (2006): 61-67 Abstract accessed on Aug. 28, 2022 {https://www.sciencedirect.com/science/article/abs/pii/S1471489205001876?via%3.Dihub}.

Langhorne, Peter, Robert Wagenaar, and Cecily Partridge. "Physiotherapy after stroke: more is better?." Physiotherapy Research International 1.2 (1996): 75-88—Abstract accessed on Aug. 28, 2022 {https://onlinelibrary.wiley.com/doi/abs/10.1002/pri.6120010204?SID=nlm%3Apub.med}.

Confavreux, Christian, and Sandra Vukusic. "The clinical course of multiple sclerosis." Handbook of clinical neurology 122 (2014): 343-36988—Abstract accessed on Aug. 28, 2022 {https://www.sciencedirect.com/science/article/abs/pii/B9780444520012000145}.

An International Preliminary Report on Patentability dated May 17, 2022, which issued during the prosecution of Applicant's PCT/IL2020/051193.

Grassi, Guido, et al. "Primary and secondary prevention of stroke by antihypertensive treatment in clinical trials." Current Hypertension Reports 4.9 (2007): 299-304—Abstract accessed on Aug. 28, 2022 {https://www.infona.pl/resource/bwmetal.element.springer-9a72e8b8-1938-3d20-.8751-425d3674a3e9}.

An Office Action dated Oct. 20, 2021, which issued during the prosecution of Australian Patent Application No. 2017323663.

(56)          References Cited

OTHER PUBLICATIONS

An Office Action dated Jul. 27, 2021, which issued during the prosecution of Indian Patent Application No. 201917013336.

Rudick, Richard A., and Susan E. Goelz. "Beta-interferon for multiple sclerosis." .Experimental cell research 317.9 (2011): 1301-1311—Abstract.

Seltzer, Ben. "Donepezil: a review." Expert opinion on drug metabolism & toxicology 1.3 (2005): 527-536—Abstract accessed on Aug. 28, 2022 .{https://www.tandfonline.com/doi/abs/10.1517/17425255.1.3.527}.

U.S. Appl. No. 63/079,496, filed Sep. 17, 2020.

U.S. Appl. No. 63/183,112, filed May 3, 2021.

U.S. Appl. No. 63/071,599, filed Aug. 28, 2020.

Requisition by the Examiner Dated Oct. 16, 2023 From the Innovation, Science and Economic Development Canada, Canadian Intellectual Property Office Re. Application No. 3,034,752. (5 Pages).

English Summary Dated May 15, 2023 of Notification of Office Action Dated May 6, 2023 From the State Intellectual Property Office of the People's Republic of China Re. Application No. 201780068350.3. (2 pages).

Communication Pursuant to Article 94(3) EPC Dated Jun. 13, 2025 From the European Patent Office Re. Application No. 20899302.2 (9 Pages).

Decision on Rejection Dated Jul. 27, 2023 From the State Intellectual Property Office of the People's Republic of China Re. Application No. 201780068350.3. (5 Pages).

Hearing Notice Dated Jan. 11, 2024 From the Government of India, Intellectual Property India, The Patent Office Re. Application No. 201917013336. (2 Pages).

Hearing Notice Dated Jan. 12, 2024 From the Government of India, Intellectual Property India, The Patent Office Re. Application No. 2133/DELNP/2014. (4 Pages).

Notice of Reason for Rejection Dated Mar. 7, 2017 From the Japan Patent Office Re. Application No. 2014-530377. (4 Pages).

Notice of Reason for Rejection Dated May 23, 2016 From the Japan Patent Office Re. Application No. 2014-530377. (4 Pages).

Notification of Decision of Grant Dated Oct. 17, 2017 From the Japan Patent Office Re. Application No. 2014-530377. (3 Pages).

English Summary Dated Aug. 8, 2023 of Decision on Rejection Dated Jul. 27, 2023 From the State Intellectual Property Office of the People's Republic of China Re. Application No. 201780068350.3. (3 pages).

Machine Translation Dated Aug. 14, 2023 of Decision on Rejection Dated Jul. 27, 2023 From the State Intellectual Property Office of the People's Republic of China Re. Application No. 201780068350.3. (5 pages).

Communication Pursuant to Article 94(3) EPC Dated Jul. 25, 2017 From the European Patent Office Re. Application No. 12831890.4 (3 Pages).

Grounds of Reason of Rejection Dated Dec. 19, 2018 From the Korean Intellectual Property Office Re. Application No. 10-2001897 (6 pages).

International Preliminary Report on Patentability Dated Mar. 18, 2014 From the International Bureau of WIPO Re. Application No. PCT/IL2012/000255. (5 Pages).

Notification of Office Action and Search Report Dated Oct. 17, 2022 From the State Intellectual Property Office of the People's Republic of China Re. Application No. 201780068350.3 and its Summary in English. (10 Pages).

Notification of Office Action Dated Jan. 27, 2016 From the State Intellectual Property Office of the People's Republic of China Re. Application No. 201280055647.3 (3 pages).

Notification of Office Action Dated May 28, 2015 From the State Intellectual Property Office of the People's Republic of China Re. Application No. 201280055647.3. (4 pages).

Translation of Notification of Office Action and Search Report Dated Oct. 17, 2022 From the State Intellectual Property Office of the People's Republic of China Re. Application No. 201780068350.3. (6 Pages).

Notification of Office Action Dated May 6, 2023 From the State Intellectual Property Office of the People's Republic of China Re. Application No. 201780068350.3. (5 Pages).

Examination Report Dated Aug. 11, 2025 From the Australian Government, IP Australia Re. Application No. 2020399308. (5 Pages).

Examination Report Under Sections 12 & 13 of the Patents Act, 1970 and the Patents Rules, 2003 Dated Sep. 24, 2025 From the Government of India, Intellectual Property India, Patents, Designs, Trade Marks, Geographical Indications, The Patent Office Re. Application No. 202247024813. (6 pages).

Notification of Office Action and Search Report Dated Oct. 28, 2025 From the State Intellectual Property Office of the People's Republic of China Re. Application No. 202080073123.1 with Its Summary and Machine Translation of Office Action into English. (35 Pages).

Requisition by the Examiner Dated Nov. 13, 2025 From the Innovation, Science and Economic Development Canada, Canadian Intellectual Property Office Re. Application No. 3,152,608. (6 Pages).

* cited by examiner

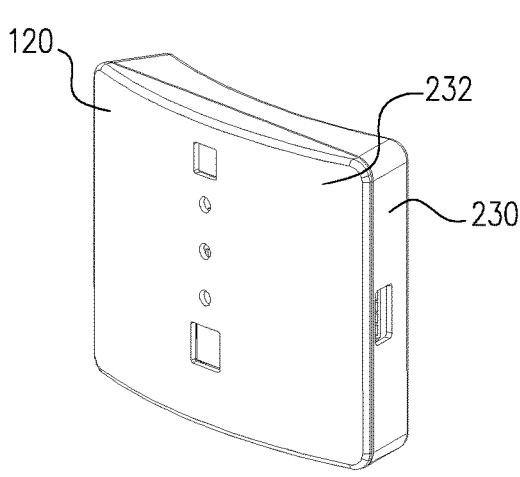
FIG. 6A
FIG. 6B
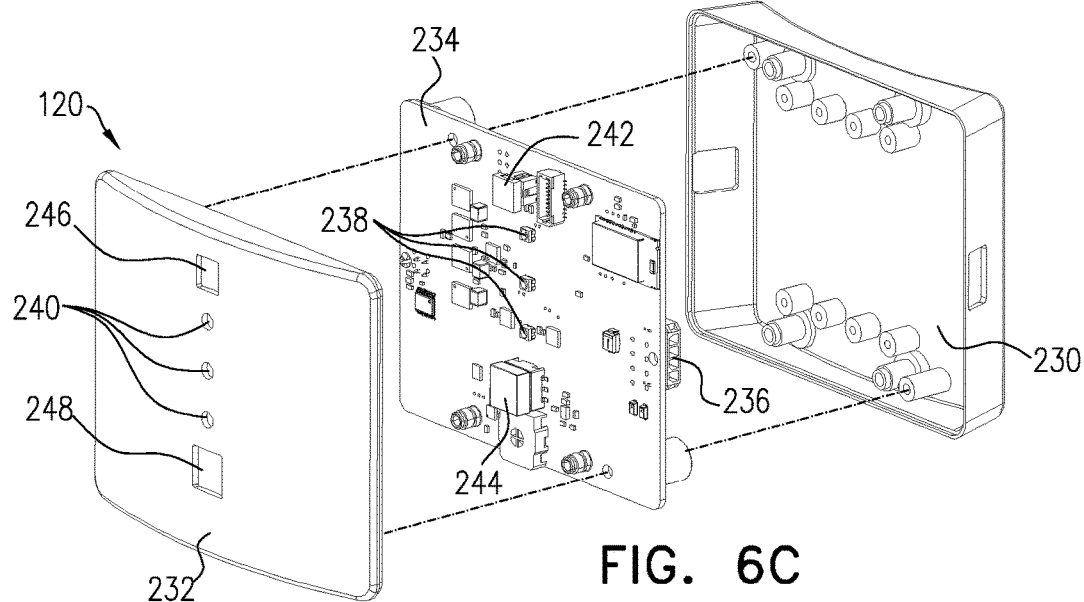
FIG. 6C
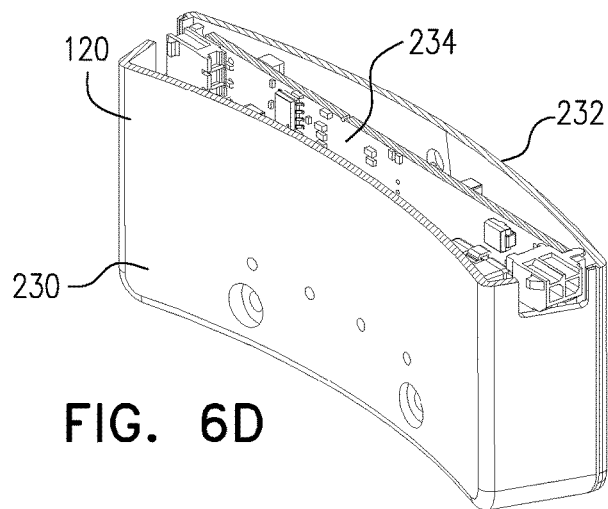
FIG. 6D

250

284

284

284

284

TREATMENT APPARATUS, SYSTEMS AND METHODS

REFERENCE TO RELATED PATENT DOCUMENTS

Reference is hereby made to the following patent documents of assignee, the contents of which are hereby incorporated by reference, which relate to the subject matter of the present invention:

U.S. Provisional Patent Application Ser. No. 62/642,037, filed Mar. 13, 2018;

U.S. Provisional Patent Application Ser. No. 62/642,038, filed Mar. 13, 2018;

U.S. Provisional Patent Application Ser. No. 62/747,671, filed Oct. 19, 2018;

U.S. Pat. No. 9,694,197, issued Jul. 4, 2017;

U.S. patent application Ser. No. 16/330,670, filed Oct. 19, 2018;

PCT Patent Application PCT/IL2017/050981, filed Mar. 5, 2019;

U.S. patent application Ser. No. 16/441,614, filed Jun. 14, 2019; and

U.S. Pat. No. 10,322,295, issued Jun. 18, 2019.

Reference is additionally made to the following U.S. patent applications of assignee, the contents of which are hereby incorporated by reference, which relate to the subject matter of the present invention and priority of which is hereby claimed:

U.S. Provisional Patent Application No. 62/946,754, filed Dec. 11, 2019 and entitled WEARABLE IOT APPARATUS FOR ELF-EMF TREATMENT ENABLING SEAMLESS CONTINUITY OF CARE; and U.S. Provisional Patent Application No. 63/071,599, filed Aug. 28, 2020 and entitled WEARABLE IOT APPARATUS FOR ELF-EMF TREATMENT ENABLING SEAMLESS CONTINUITY OF CARE.

FIELD OF THE INVENTION

The present invention relates to systems, apparatus and methods for treatment of neurological conditions and disorders of the central nervous system and more particularly to systems, apparatus and methods for treatment of neurological conditions and disorders of the central nervous system by application of electromagnetic fields thereto.

BACKGROUND OF THE INVENTION

Various systems, methods and apparatus are known for treatment of neurological disorders of the central nervous system by application of electromagnetic fields thereto.

SUMMARY OF THE INVENTION

The present invention seeks to provide improved apparatus, systems and methods for treatment of neurological disorders of the central nervous system.

There is thus provided in accordance with a preferred embodiment of the present invention body wearable treatment apparatus for treatment of neurological disorders and conditions of the central nervous system by application of electromagnetic fields thereto, the apparatus including a coil mounting portion and a body mounting portion, the coil mounting portion being removably mounted on the body mounting portion.

In accordance with a preferred embodiment of the present invention the coil mounting portion is selectably positionable relative to the body mounting portion.

Preferably, the body wearable treatment apparatus for treatment of neurological disorders and conditions of the central nervous system by application of electromagnetic fields thereto also includes an electronic control unit.

In accordance with a preferred embodiment of the present invention the coil mounting portion includes a coil support substrate, formed to define a head surrounding portion and a back portion, and an electromagnetic field generating coil mounted onto the coil support substrate.

Preferably, the electromagnetic field generating coil is a single coil, which is connected to the electronic control unit at opposite ends thereof. Additionally or alternatively, the electromagnetic field generating coil is formed of a flat braided conductor.

In accordance with a preferred embodiment of the present invention the electromagnetic field generating coil is arranged in interconnected upper and lower electromagnetic field generating coil winding portions. Additionally or alternatively, the electromagnetic field generating coil includes multiple coil windings, which are retained in a mutually stacked orientation by connectors.

In accordance with a preferred embodiment of the present invention the upper electromagnetic field generating coil winding portion extends along the coil support substrate adjacent a top edge of the head surrounding portion and up and down along a length of the back portion at an interior thereof. Preferably, the lower electromagnetic field generating coil winding portion extends along the coil support substrate adjacent a bottom edge of the head surrounding portion thereof and up and down along a length of the back portion adjacent an edge thereof.

In accordance with a preferred embodiment of the present invention the control unit provides at least one of the following functions: communication with an external server which stores treatment protocols so as to download specific treatment protocols for a given patient at a given time, wave generation functionality operative to control application of current to the electromagnetic field generating coil in accordance with the specific treatment protocols for a given patient at a given time and feedback functionality operative to provide feedback confirming progress of the specific treatment protocols. More preferably, the control unit provides at least two of the following functions: communication with an external server which stores treatment protocols so as to download specific treatment protocols for a given patient at a given time, wave generation functionality operative to control application of current to the electromagnetic field generating coil in accordance with the specific treatment protocols for a given patient at a given time and feedback functionality operative to provide feedback confirming progress of the specific treatment protocols. Most preferably, the control unit provides all of the following functions: communication with an external server which stores treatment protocols so as to download specific treatment protocols for a given patient at a given time, wave generation functionality operative to control application of current to the electromagnetic field generating coil in accordance with the specific treatment protocols for a given patient at a given time and feedback functionality operative to provide feedback confirming progress of the specific treatment protocols.

In accordance with a preferred embodiment of the present invention the body mounting portion includes a flexible band with a narrowed portion formed at a rear portion thereof. Additionally, the coil mounting portion includes a channel through which the flexible band extends, thereby providing selectable vertical positioning of the coil mounting portion onto the body mounting portion.

In accordance with a preferred embodiment of the present invention the body mounting portion comprises a shoulder strap. Additionally, the shoulder strap is configured to position the coil mounting portion relative to a patient.

There is also provided in accordance with another preferred embodiment of the present invention a system for treatment of neurological disorders and conditions of the central nervous system by application of electromagnetic fields thereto, the system including at least one database storing information relating to treatment protocols, a server communicating with the at least one database and body wearable treatment apparatus communicating with the server, the body wearable treatment apparatus including a coil mounting portion and a body mounting portion, the coil mounting portion being removably mounted on the body mounting portion.

In accordance with a preferred embodiment of the present invention the system for treatment of neurological disorders and conditions of the central nervous system by application of electromagnetic fields thereto also includes sensors for sensing real time sensed patient parameters. Preferably, the sensors are mounted on removably wearable substrates. Additionally, the removably wearable substrates are selected from a helmet and a glove.

BRIEF DESCRIPTION OF THE DRAWINGS

The present invention will be understood and appreciated more fully from the following detailed description, taken in conjunction with the drawings in which:

FIGS. 6A and 6B are simplified pictorial view illustrations, taken from different perspectives, of a control assembly forming part of the apparatus of FIGS. 1A-2B;

FIGS. 6C and 6D are simplified respective exploded view and sectional view illustrations of the control assembly of FIGS. 6A and 6B, FIG. 6D being taken along lines 6D-6D in FIG. 6B;

DETAILED DESCRIPTION OF PREFERRED
EMBODIMENTS

The system and apparatus of the present invention enable patients to receive electromagnetic field (EMF) treatments, during the process of recovery, in different places, such as in a hospital, a clinic, a care center, a rehabilitation facility, their own home or any other suitable location, in a comfortable and suitable position. Additionally, the system and apparatus of the present invention enable the patient to participate in other activities, such as physiotherapy, occupational therapy and cognitive training, during the EMF treatment.

Reference is now made to FIGS. 1A-12B, which are simplified pictorial illustrations of a preferred embodiment of body wearable treatment apparatus 100, for treatment of neurological disorders and conditions of the central nervous system by application of electromagnetic fields thereto.

Figure 9A:
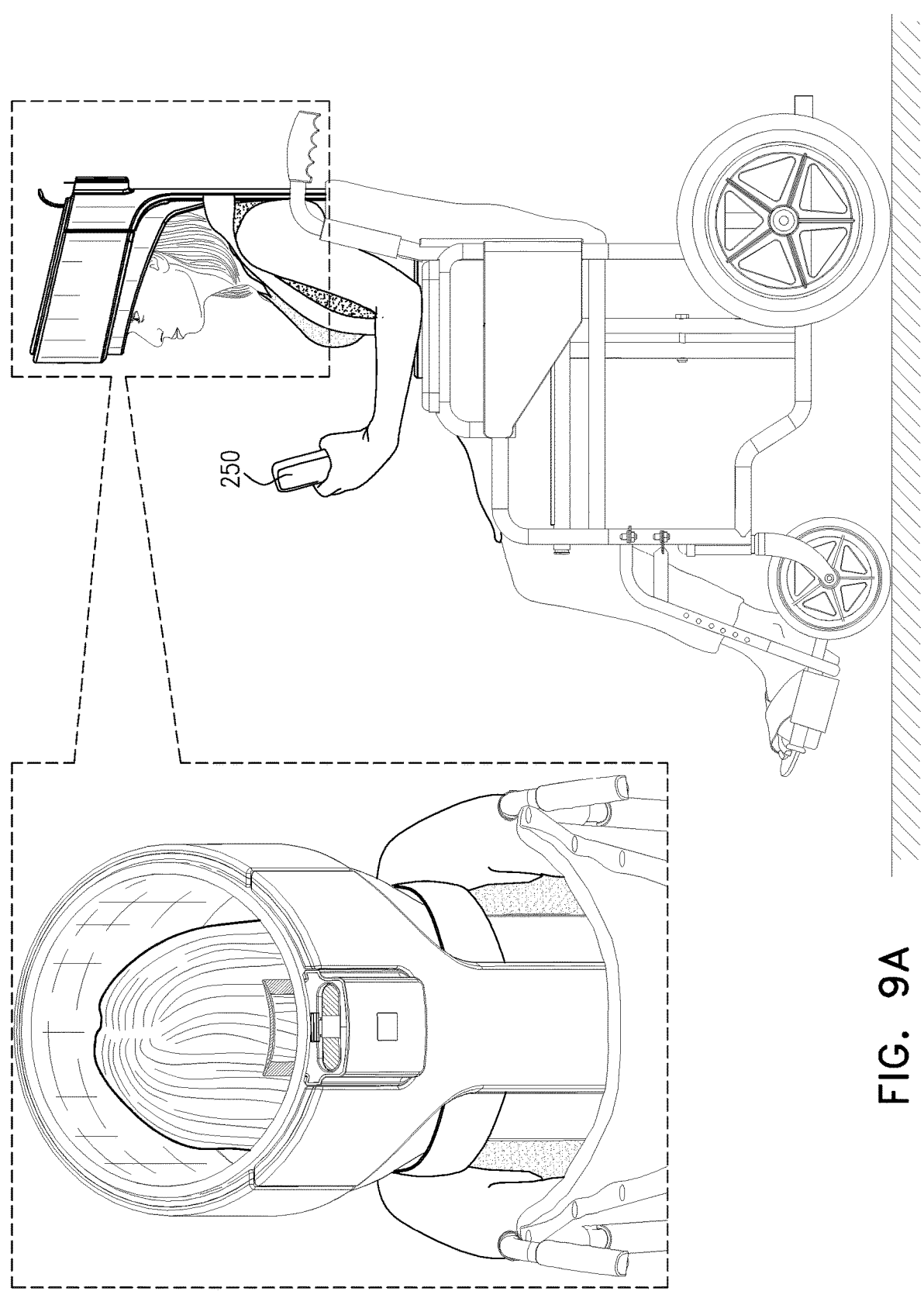
FIGS. 9A & 9B are simplified side view pictorial illustrations of the apparatus of FIGS. 1A-8B being worn by a wheelchair-bound patient and being controlled via a cell-phone app, as well as sensor assemblies which may also be worn by the wheelchair-bound patient.
Figure 9B:
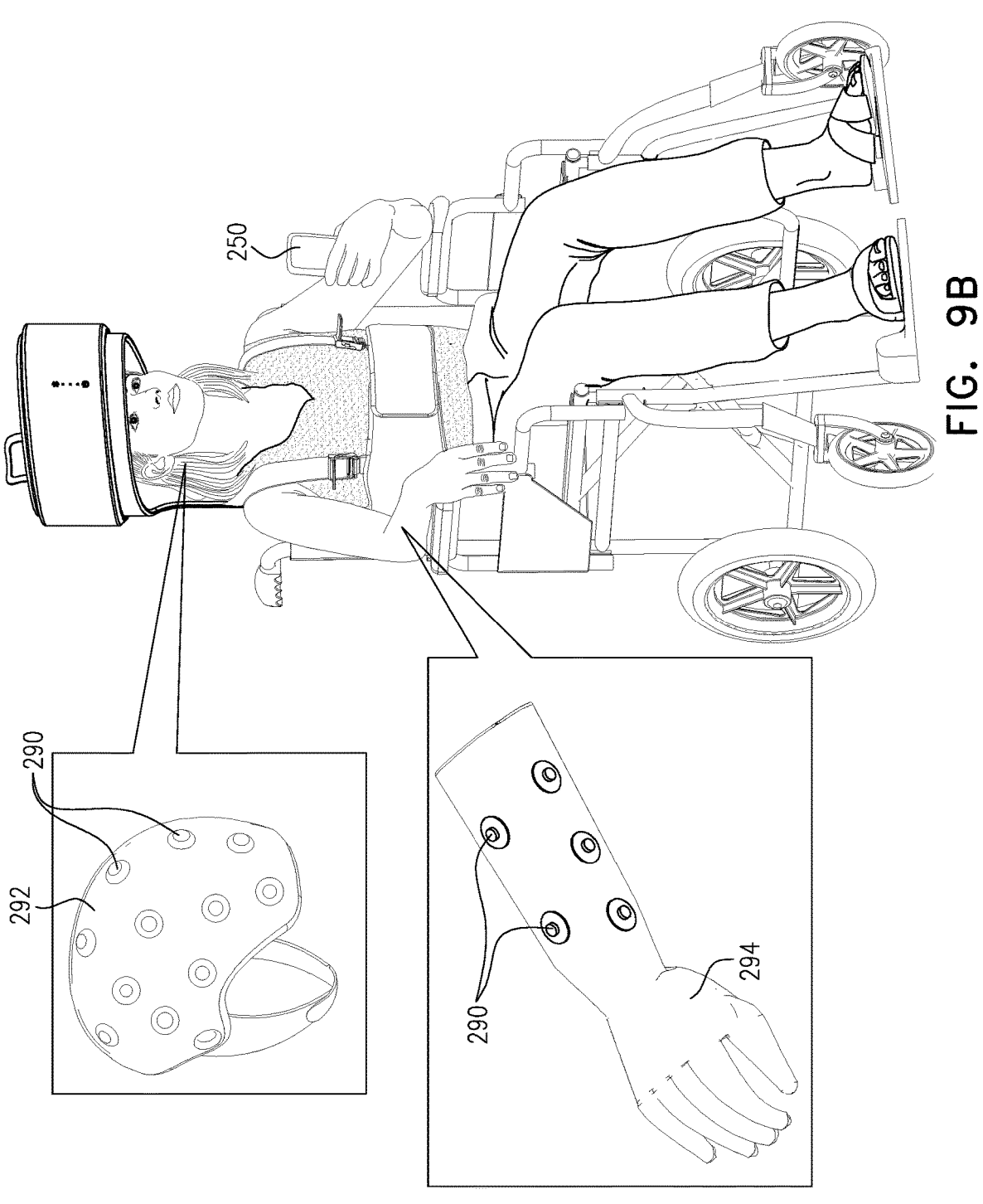
Figures 10A, 10B:
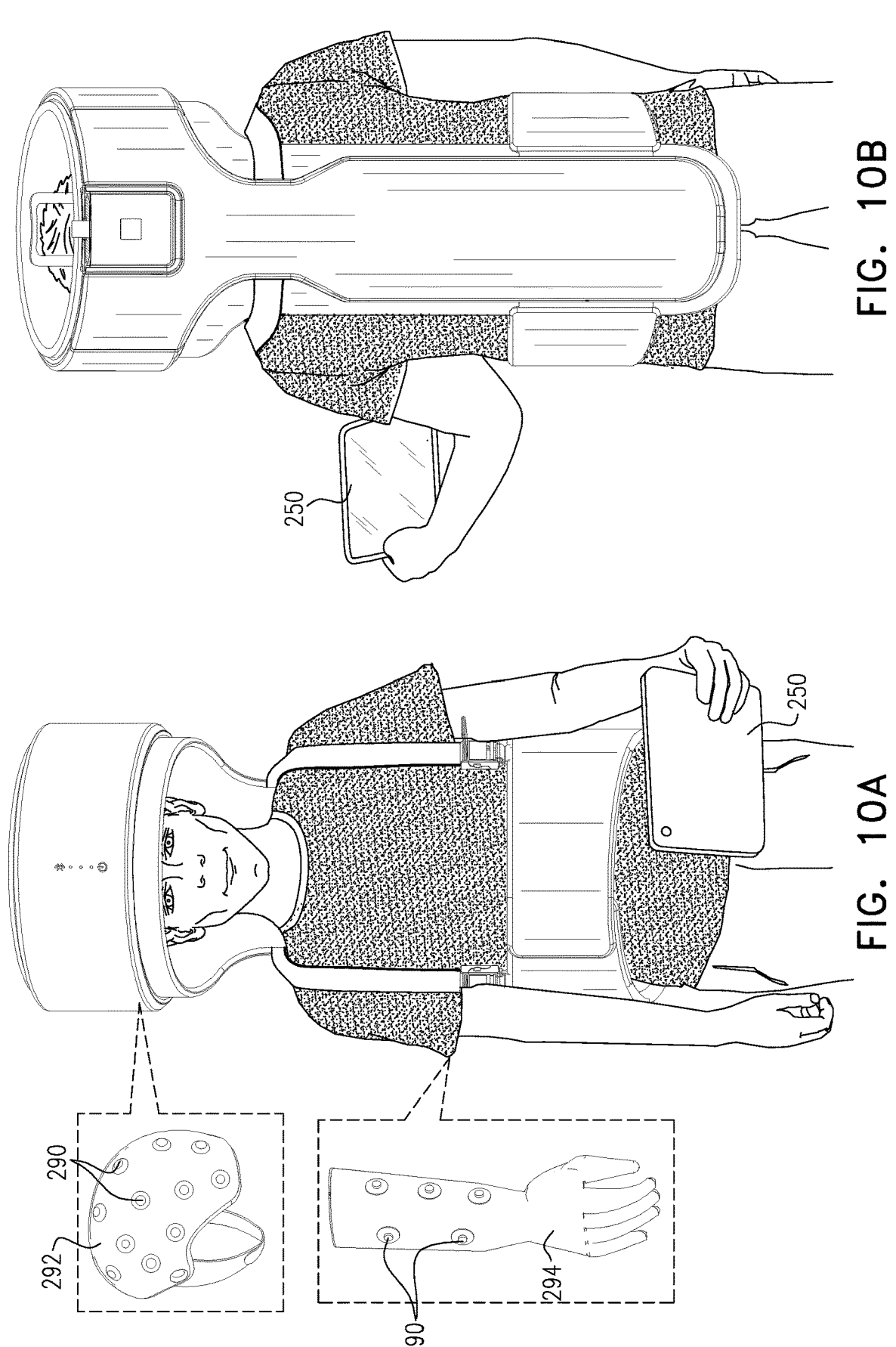
FIGS. 10A & 10B are simplified side view pictorial view illustrations of the apparatus of FIGS. 1A-8B being worn by a standing patient and being controlled via a tablet app, as well as sensor assemblies which may also be worn by the standing patient.
Figures 11A, 11B:
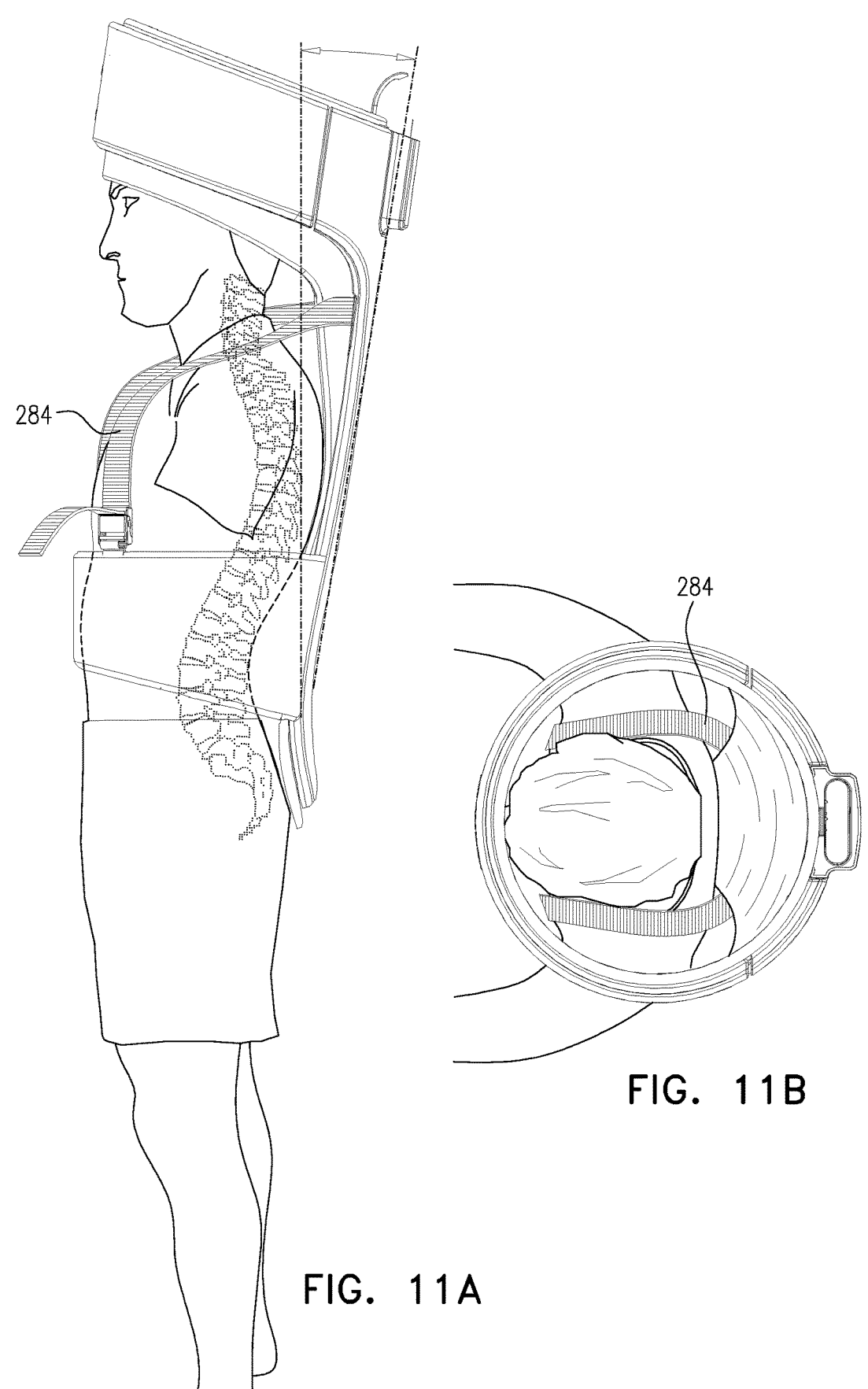
FIGS. 11A & 11B are simplified respective side view and top view illustrations of the apparatus of FIGS. 1A-8B being worn by a standing patient in a first operative orientation.
Figures 12A, 12B:
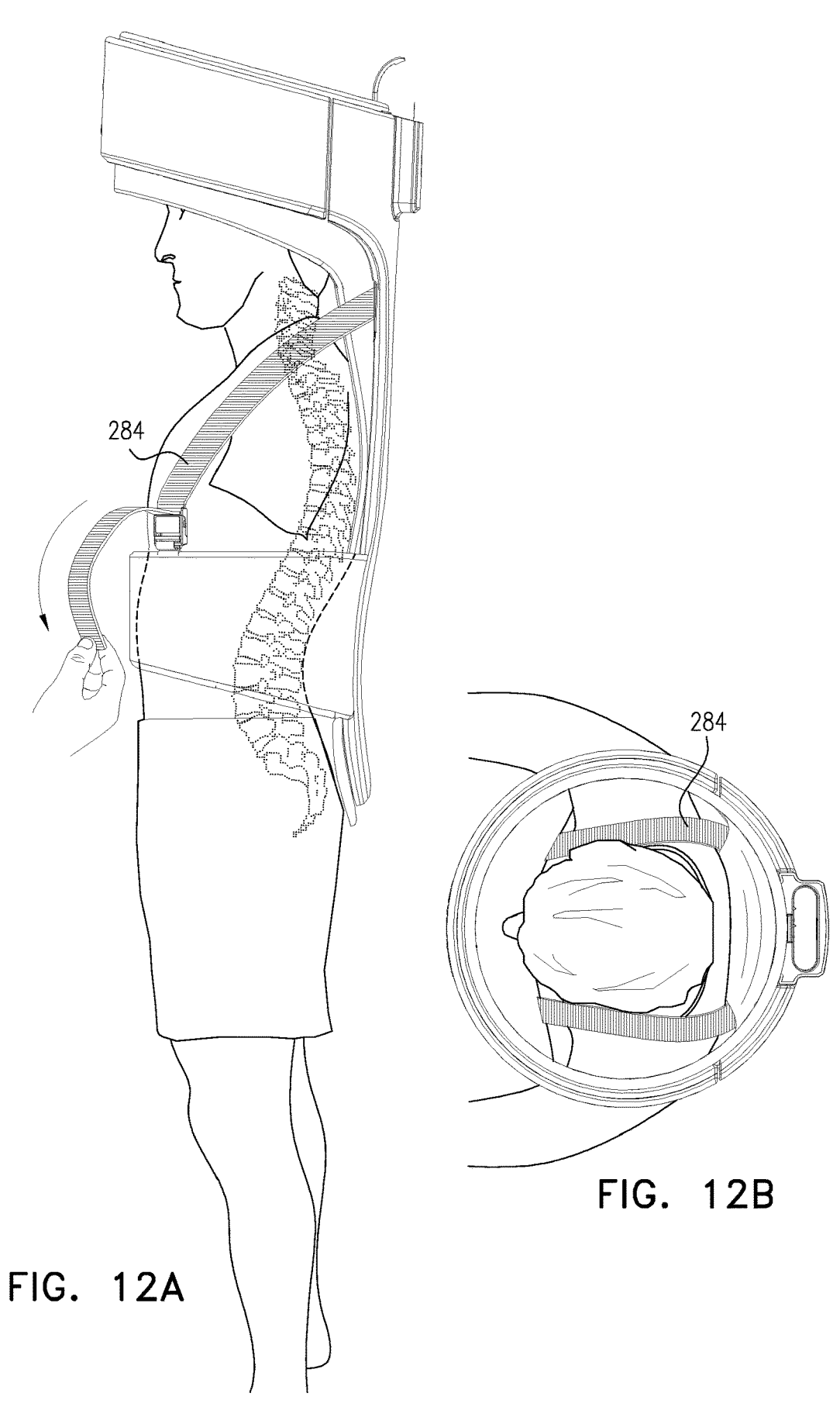
FIGS. 12A & 12B are simplified respective side view and top view illustrations of the apparatus of FIGS. 1A-8B being worn by a standing patient in a second operative orientation.

FIGS. 9A & 9B are simplified pictorial illustrations of an embodiment of apparatus 100, as worn by a wheel-chair bound patient, for treatment of neurological disorders of the central nervous system by application of electromagnetic fields thereto. FIGS. 10A and 10B are simplified pictorial illustrations of an embodiment of body wearable treatment apparatus 100, as worn by a standing patient. FIGS. 9B and 10A also illustrate sensors, such as EEG and EMG sensors, which may be mounted onto a helmet and/or a glove, worn by the patient prior to, during and following treatment. It is appreciated that the sensors may also be directly mounted on the patient's skin.

As seen in FIGS. 1A-8B, body wearable treatment apparatus 100 includes a coil mounting portion 102 and a body mounting portion 104, the coil mounting portion 102 preferably being removably mounted onto, selectably positioned onto and supported by the body mounting portion 104. The structure of the coil mounting portion 102 is illustrated particularly in FIGS. 1A-7D and the structure of the body mounting portion 104 is illustrated particularly in FIGS. 8A & 8B.

Figure 1A:
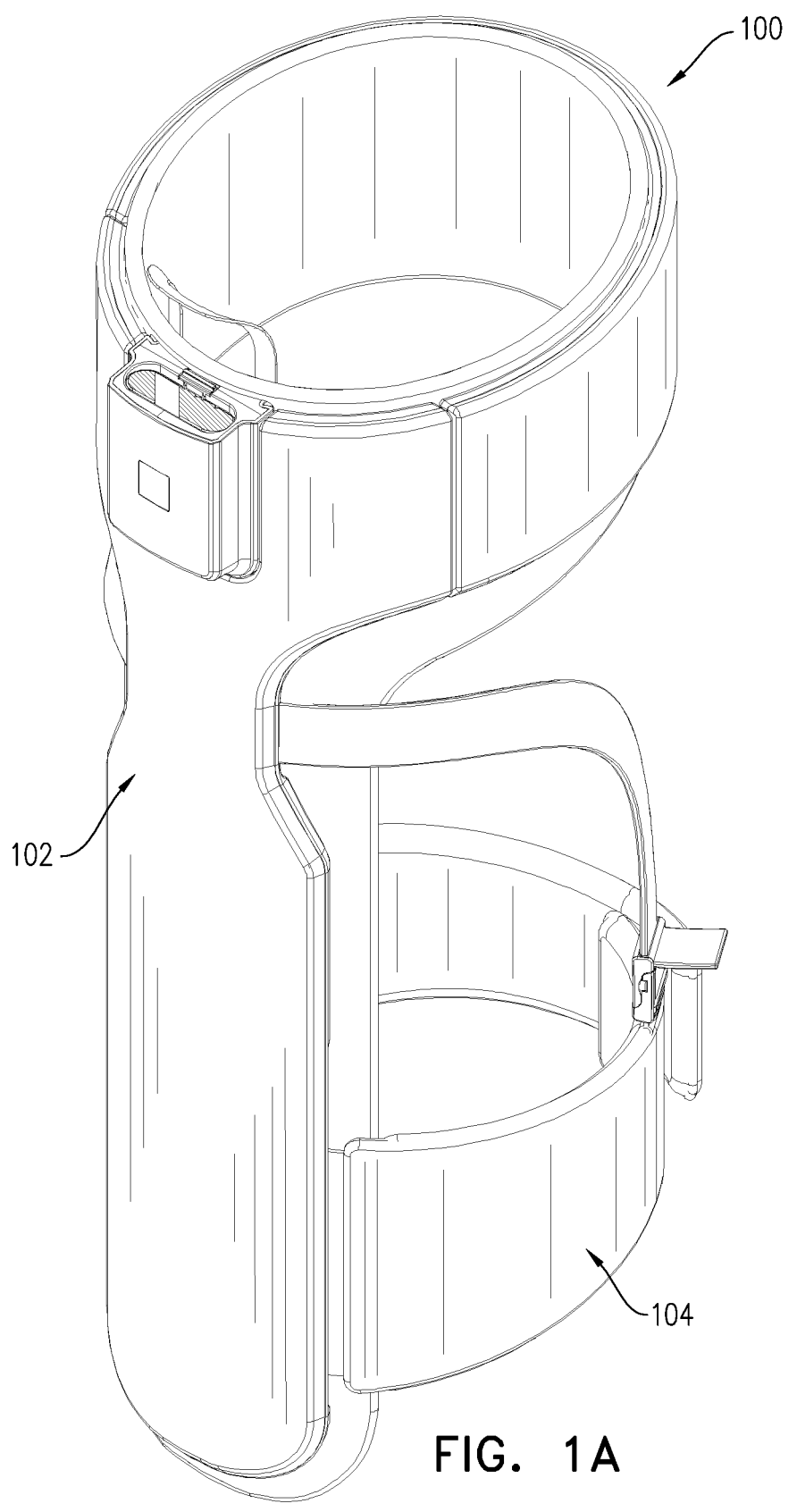
FIGS. 1A and 1B are simplified pictorial illustrations, taken from different perspectives, of an embodiment of apparatus for treatment of neurological disorders of the central nervous system by application of electromagnetic fields thereto, constructed and operative in accordance with a preferred embodiment of the present invention.
Figure 1B:
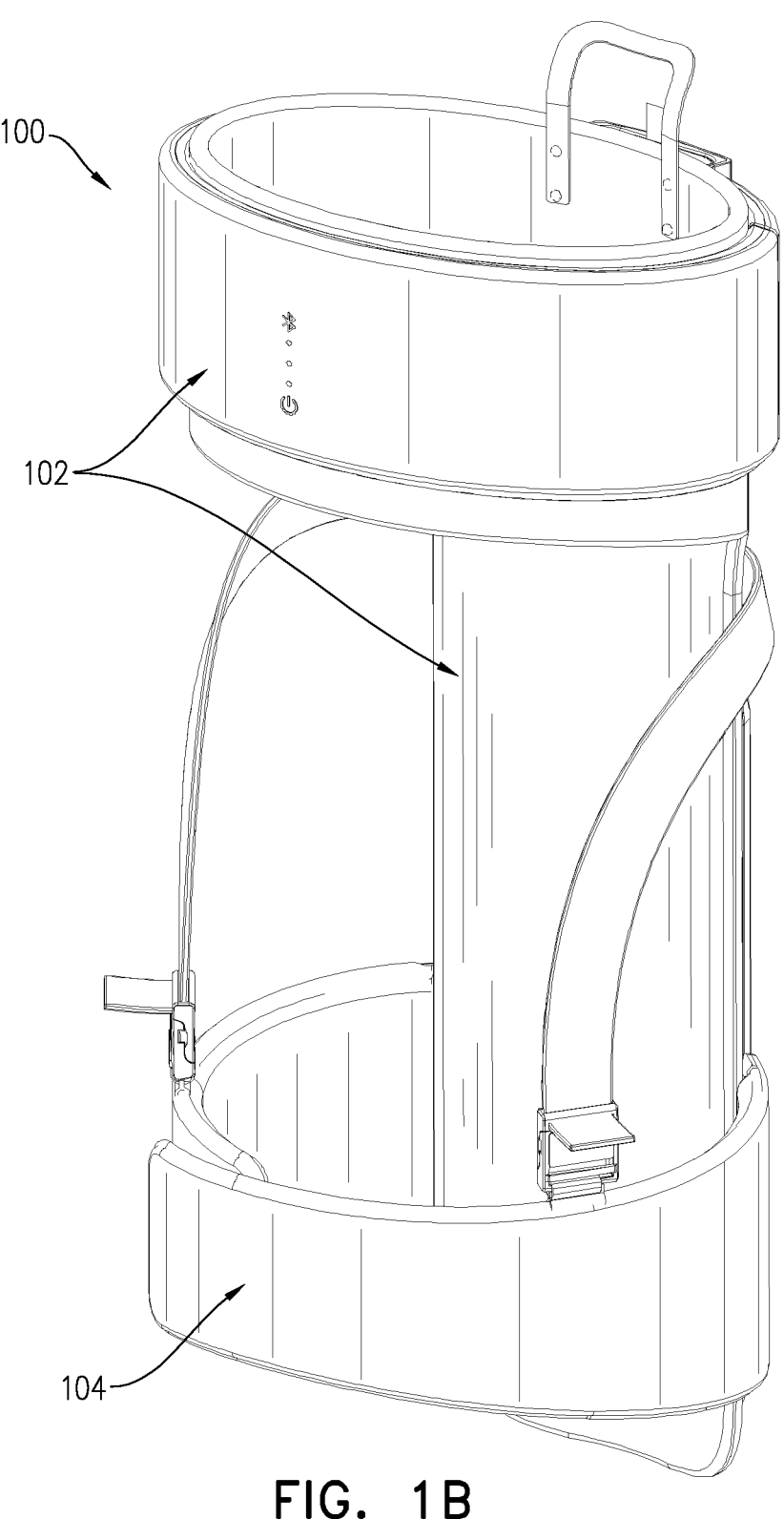
Figure 2A:
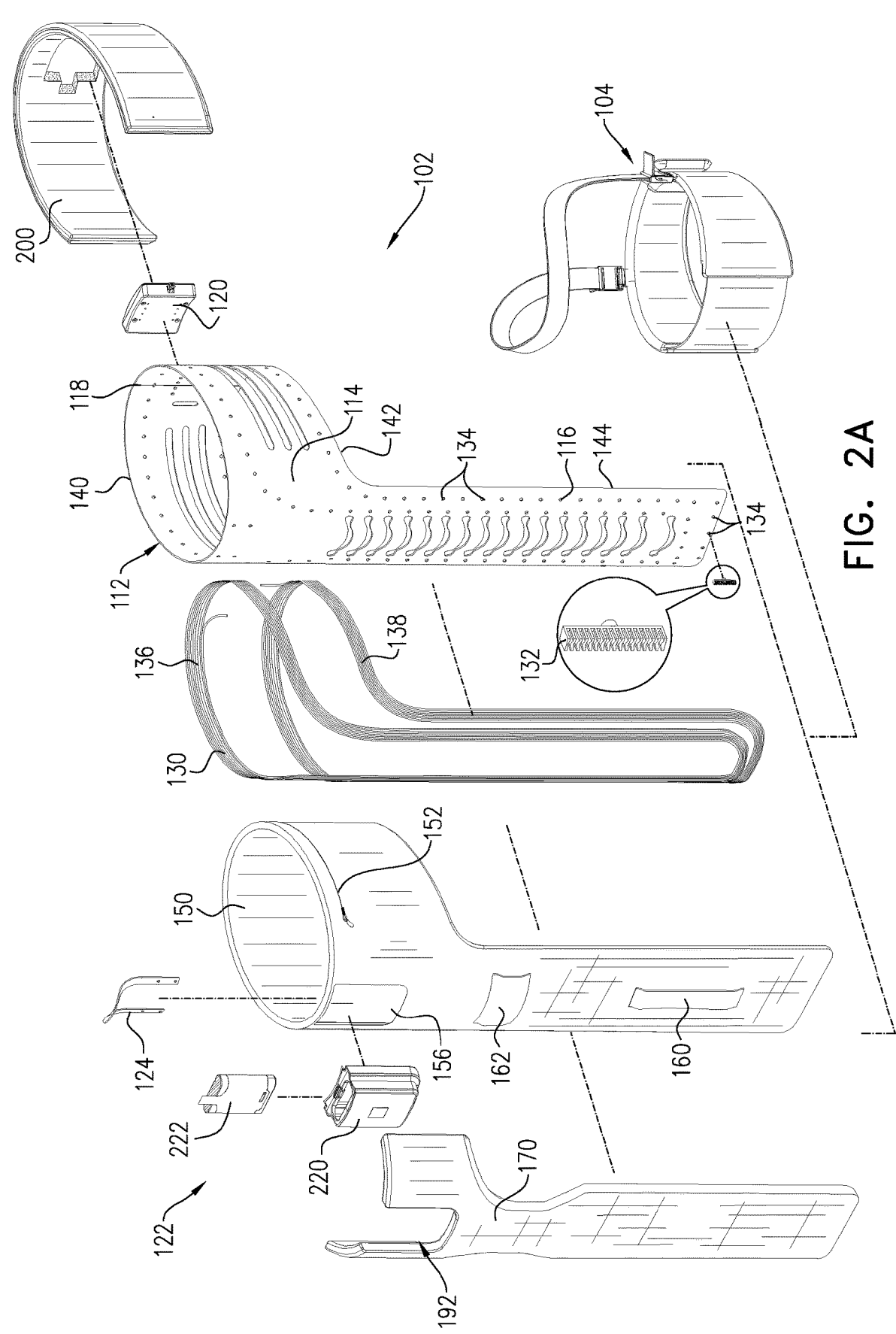
FIGS. 2A and 2B are simplified exploded view illustrations, taken from different perspectives, of the apparatus of FIGS. 1A & 1B.
Figure 2B:
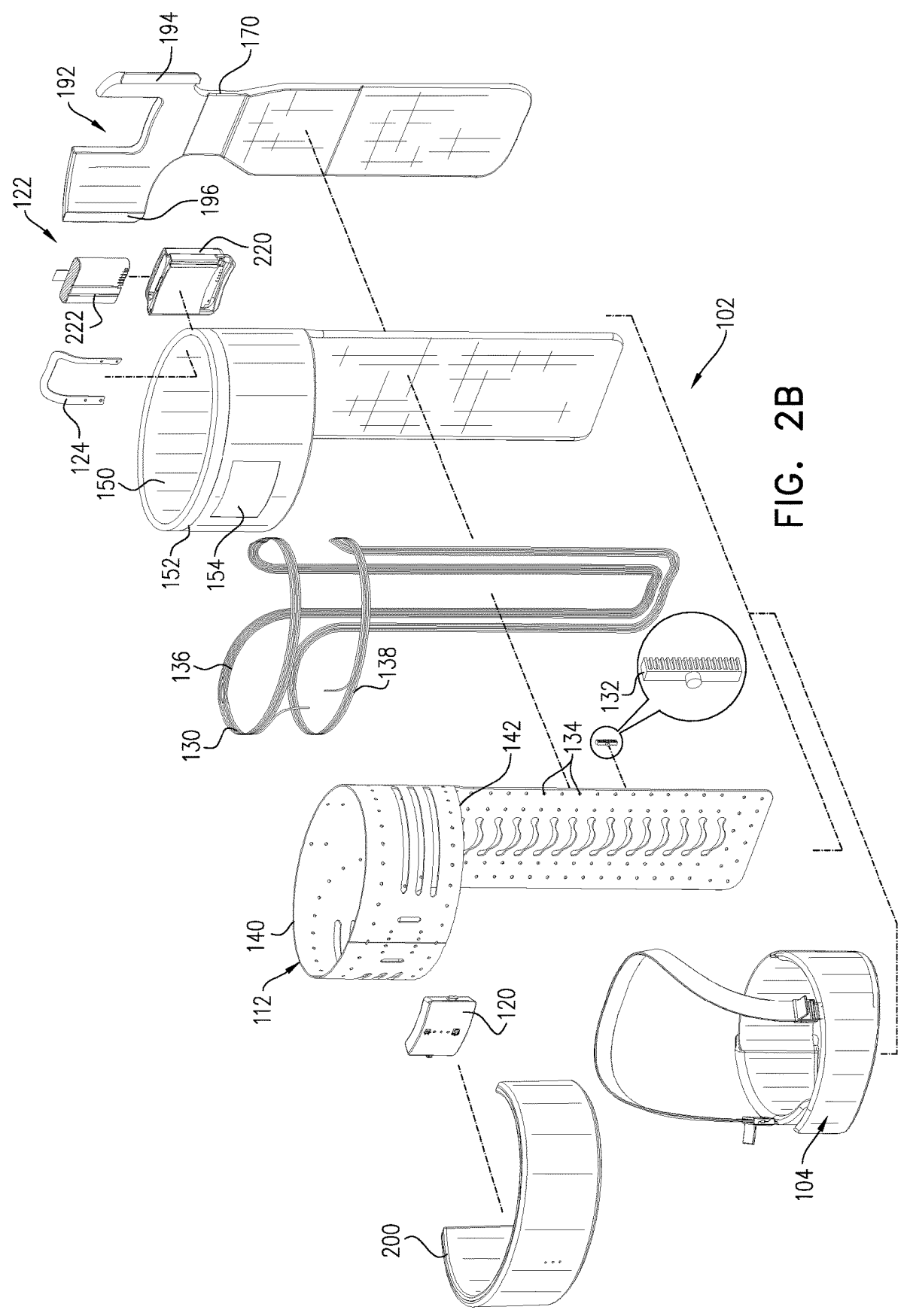
Figure 3A:
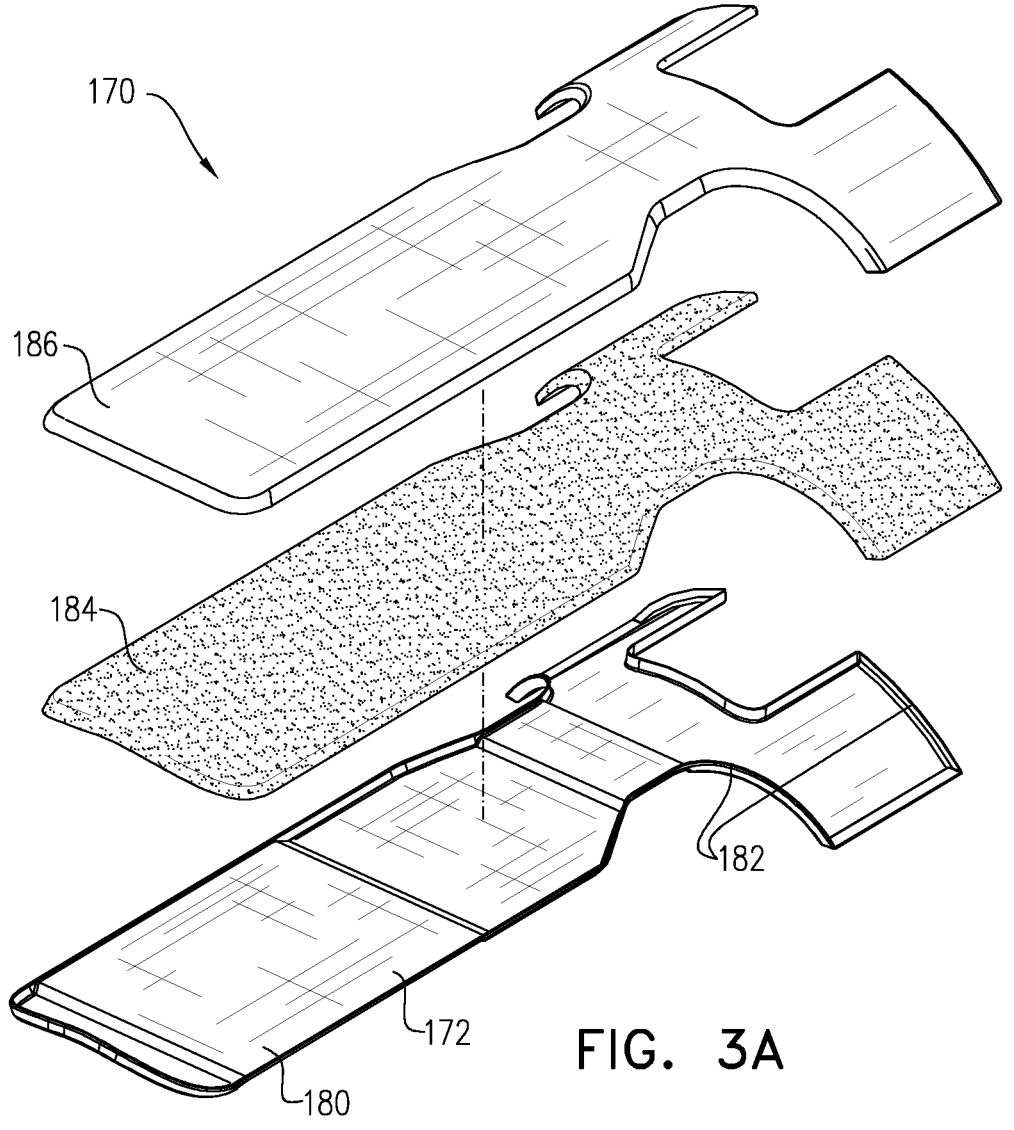
FIGS. 3A, 3B, 3C and 3D are, respectively, a simplified exploded view, first and second simplified pictorial views and a simplified sectional view illustration of a back cover assembly forming part of the apparatus of FIGS. 1A-2B, FIG. 3D being taken along lines 3D-3D in FIG. 3C.
Figures 3B, 3C, 3D:
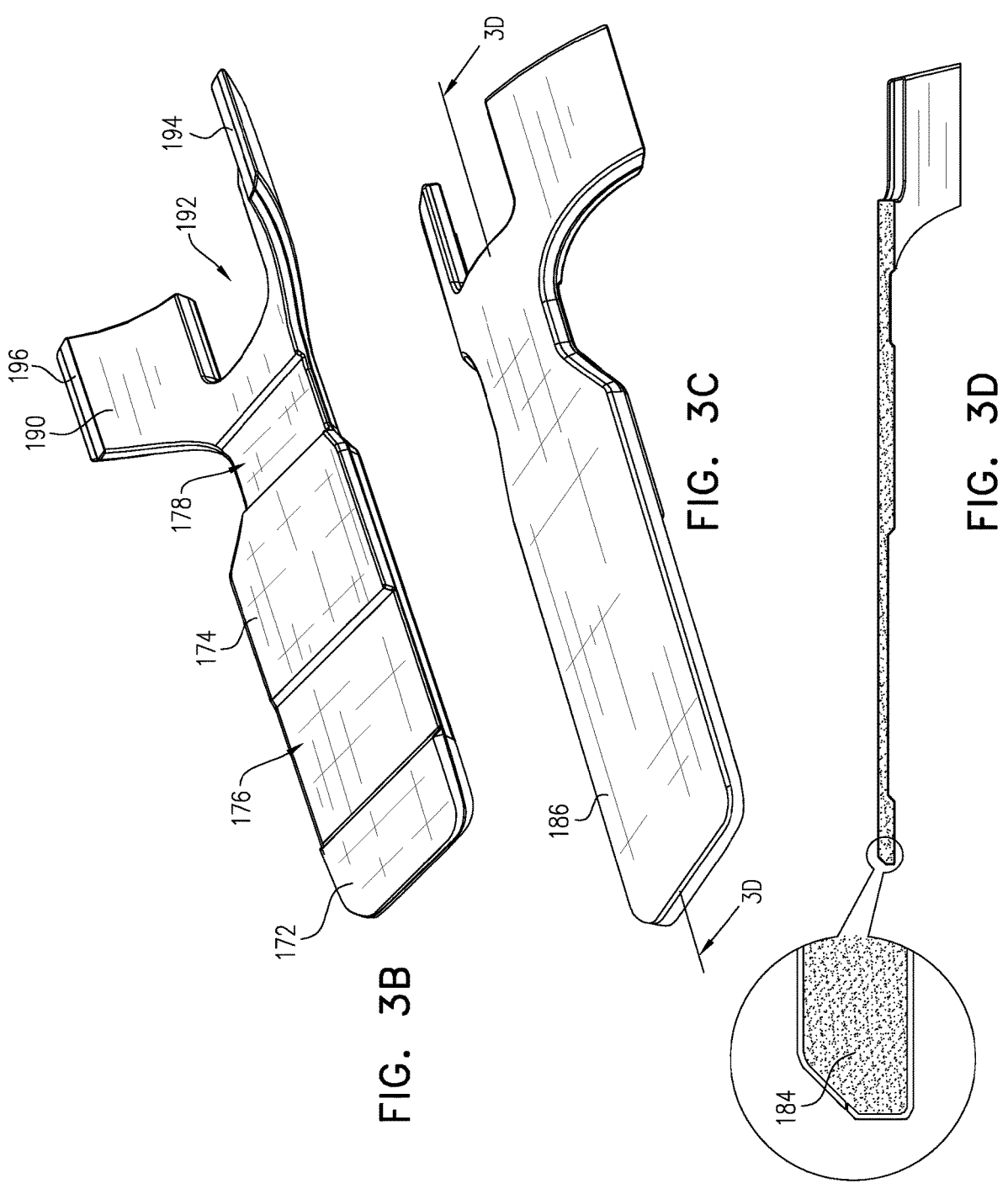
Figures 4A, 4B, 4C, 4D, 4E:
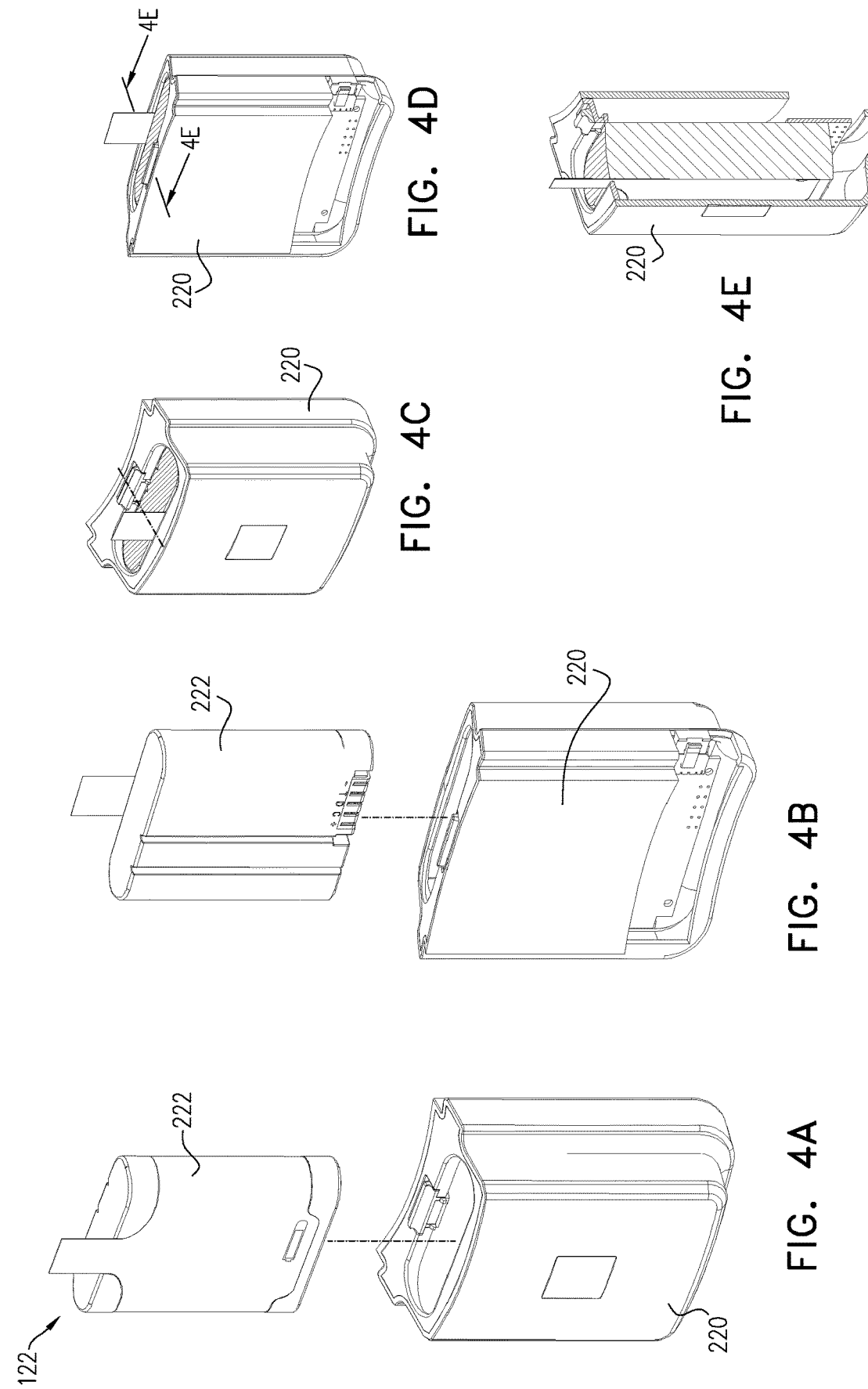
FIGS. 4A and 4B are simplified exploded view illustrations, taken from different perspectives, of a battery assembly forming part of the apparatus of FIGS. 1A-2B.
FIGS. 4C, 4D and 4E are simplified respective first and second pictorial illustrations and a sectional illustration of the battery assembly of FIGS. 4A and 4B, FIG. 4E being taken along lines 4E-4E in FIG. 4D.

Referring initially to FIGS. 1A-7D and more specifically to the exploded view illustrations of FIGS. 2A & 2B, it is seen that the coil mounting portion 102 includes an integral flexible coil support substrate 112, formed of a flexible plastic material, such as a sheet of polypropylene, which is formed to define a head surrounding portion 114 and a back portion 116. The sheet of polypropylene may be seamed at the front-facing surface of head surrounding portion 114, as shown at 118, by any suitable joining technique, such as the use of clips, sewing or adhesive.

An electronic control unit 120 is preferably mounted onto the front-facing surface of head surrounding portion 114. The electronic control unit 120 is preferably battery powered by means of a battery pack 122, preferably mounted onto a rear-facing surface of head surrounding portion 114, which is connected to control unit 120 by power supply conductors (not shown). Battery pack 122 is preferably mounted onto the rear-facing surface of head surrounding portion 114 together with a handle 124.

An electromagnetic field generating coil 130 is preferably mounted onto an outer surface of support substrate 112 by means of plastic connectors 132, which engage apertures 134 formed in support substrate 112, and is galvanically connected at first and second ends thereof (not shown) to control unit 120. Electromagnetic field generating coil 130 is preferably a single braided flat coil, such as a flat bare braided copper wire having a cross section of 1.5 mm$^2$, made from 2*16 gauge 32 wires, for example a model TZX, manufactured by Zhejuand Bridgold Copper Tech Co. Ltd, China, and is arranged in interconnected respective upper and lower electromagnetic field generating coil winding portions 136 and 138.

Upper electromagnetic field generating coil winding portion 136 preferably includes approximately 16 coil windings, which are retained in a mutually stacked orientation by connectors 132, which engage apertures 134 formed on support substrate 112. Lower electromagnetic field generating coil winding portion 138 preferably includes approximately 12 coil windings, which are retained in a mutually stacked orientation by connectors 132, which engage apertures 134.

Upper electromagnetic field generating coil winding portion 136 extends along inner surface of support substrate 112 adjacent a top edge 140 of head surrounding portion 114 thereof and up and down along the length of the back portion 116 at an interior location thereof.

Lower electromagnetic field generating coil winding portion 138 extends along outer surface of support substrate 112 adjacent a bottom edge 142 of head surrounding portion 114 thereof and up and down along the length of the back portion 116 adjacent a peripheral edge 144 thereof.

Alternatively, electromagnetic field generating coil 130 may include multiple coils, which may each be controlled individually to generate one or more electromagnetic fields around different portions of the central nervous system of a patient. In another alternative embodiment, electromagnetic field generating coil 130 is formed as one or more conductive plates, which may each be controlled individually to generate one or more electromagnetic fields around different portions of the central nervous system of a patient.

Figures 5A, 5B:
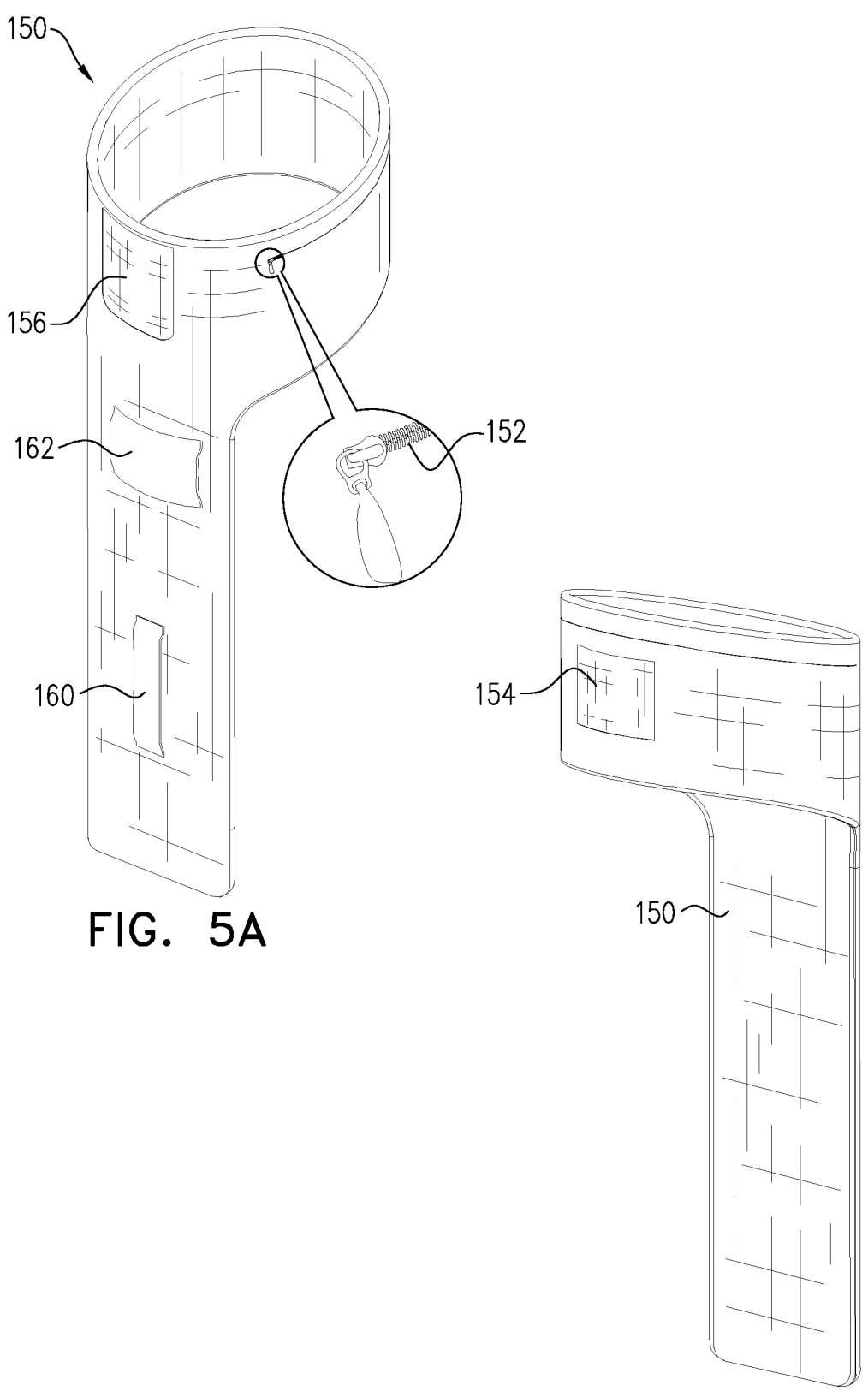
FIGS. 5A and 5B are simplified respective first and second pictorial illustrations of a flexible fabric cover forming part of the apparatus of FIGS. 1A-2B.
Figure 7A:
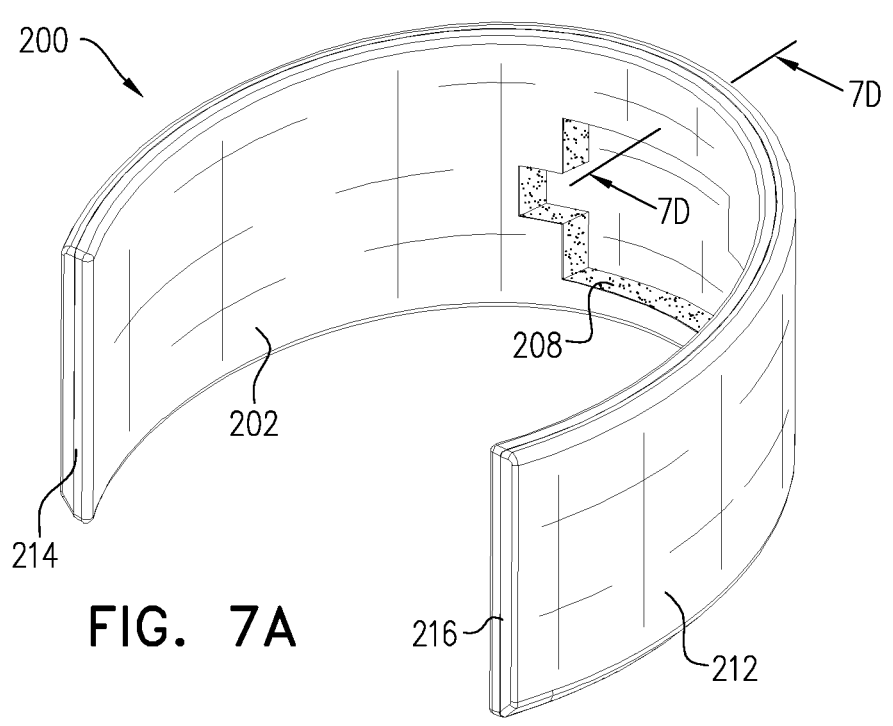
FIGS. 7A and 7B are simplified pictorial view illustrations, taken from different perspectives, of a head band assembly forming part of the apparatus of FIGS. 1A-2B.
Figure 7B:
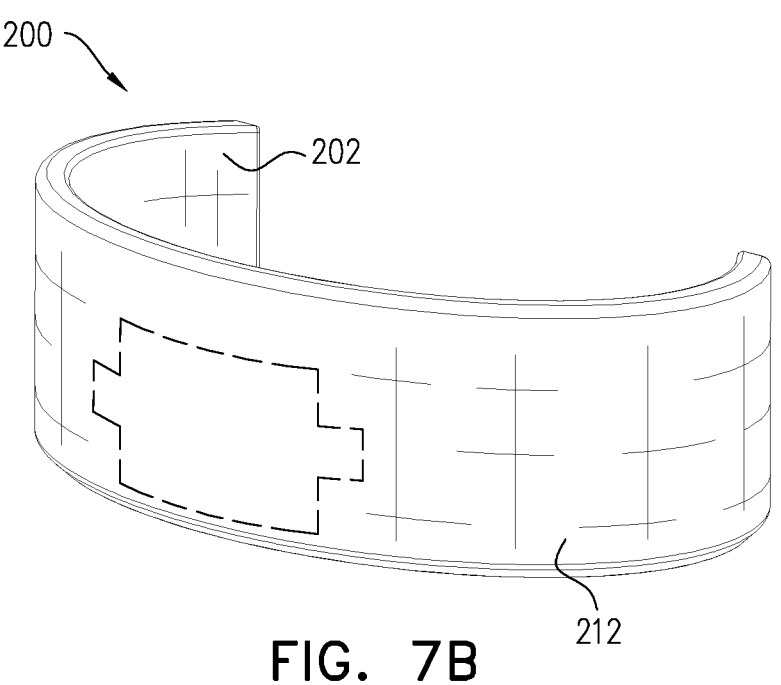
Figures 7C, 7D:
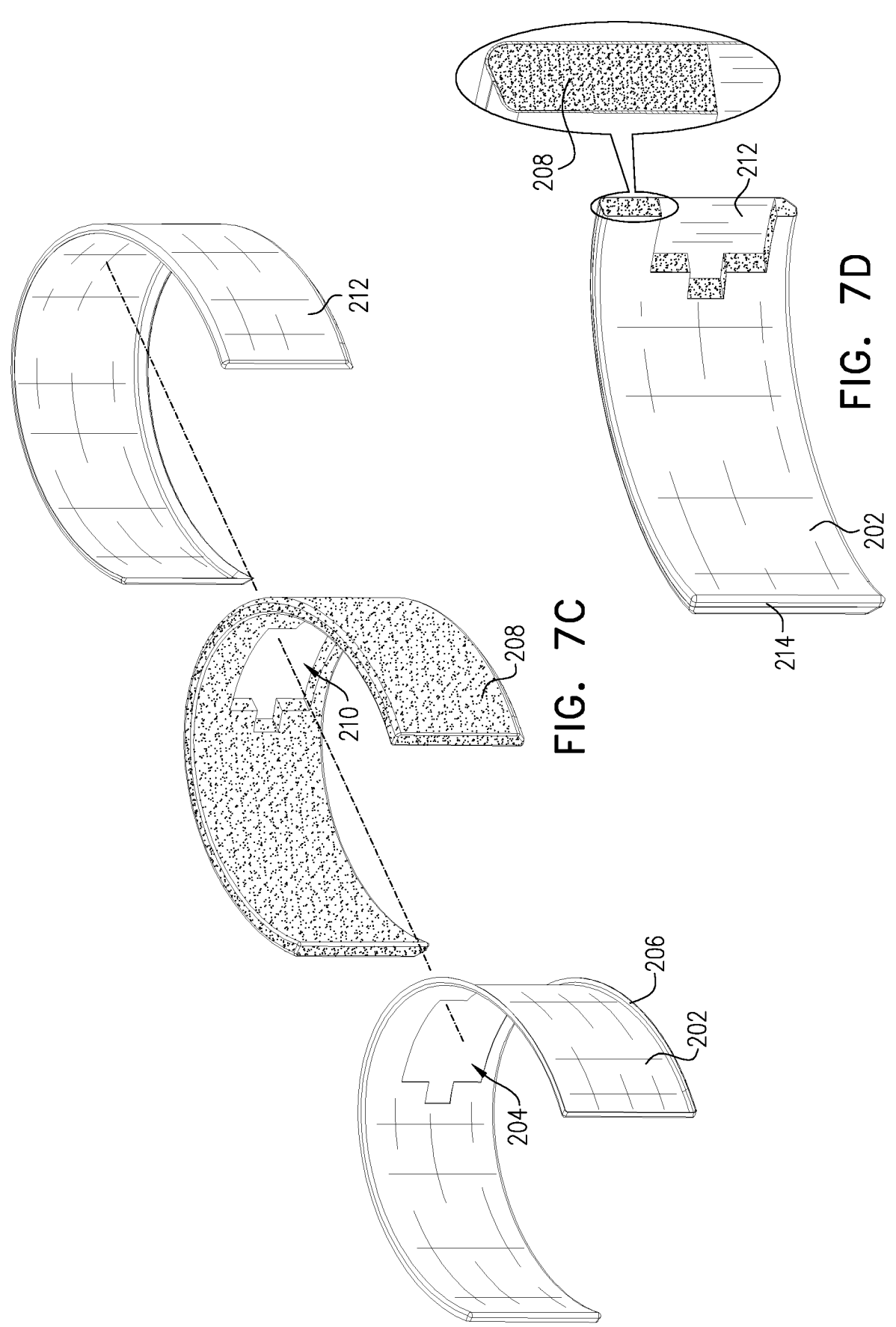
FIGS. 7C and 7D are simplified respective exploded view and sectional view illustrations of the head band assembly of FIGS. 7A and 7B, FIG. 7D being taken along lines 7D-7D in FIG. 7A.

A flexible cover 150, preferably formed of a stretchable textile material, surrounds the coil 130 and the support substrate 112 and is secured thereon by a zipper 152 or any other suitable fastener. Flexible cover 150 includes a cut out 154 for control unit 120 and a cut out 156 for battery pack 122. Flexible cover 150 is shown in FIGS. 5A & 5B, mounted over the coil 130 and the support substrate 112.

Flexible cover 150 includes a mounting channel 160 for supporting engagement with and by body mounting portion 104, as is described hereinbelow with reference to FIGS. 8A & 8B. Flexible cover 150 includes a shoulder strap mounting channel 162 for supporting engagement with and by a shoulder strap of body mounting portion 104, as is described hereinbelow with reference to FIGS. 8A & 8B.

Coil mounting portion 102 also includes a back cover assembly 170, which is illustrated in FIGS. 3A-3D. As seen in FIGS. 3A-3D, back cover assembly 170 preferably includes a substrate 172, preferably formed of a semi-rigid plastic material, which defines on a concave surface 174 thereof (FIG. 3B) a transverse recess 176 for accommodating a portion of body portion 104, which extends through mounting channel 160 of flexible cover 150. Concave surface 174 also defines a transverse recess 178 for accommodating a shoulder strap of body mounting portion 174, which extends through mounting channel 162 of flexible cover 150. Both transverse recesses 176 and 178 are configured to permit adjustable mounting of the coil mounting portion 102 relative to the body mounting portion 174.

A convex surface 180 (FIG. 3A) of substrate 172 preferably defines a raised peripheral edge 182, which accommodates a layer 184 of a flexible foamed plastic material. Formed over layer 184 and joined to substrate 172 and enclosing layer 184 is a back layer 186, preferably formed of a semi rigid plastic material.

A top portion 190 of back cover assembly 170 is preferably joined to a corresponding top portion of flexible cover 150 in any suitable manner. The remainder of back cover assembly 170 is spaced from flexible cover 150 in order to accommodate the body mounting portion 104. Top portion 190 of back cover assembly 170 is preferably formed with a cut out 192 for accommodating battery pack 122. Top portion 190 of back cover assembly 170 is formed with mutually spaced mutually facing edges 194 and 196.

A forward head portion cover assembly 200 is mounted onto head surrounding portion 114 of support substrate 112 and over flexible cover 150. As seen in FIGS. 7A-7D, forward head portion cover assembly 200 preferably includes a substrate 202, preferably formed of a semi-rigid plastic material, which is formed with a cut out 204 for accommodating control unit 120. A concave surface of substrate 202 is preferably formed with a raised peripheral edge 206, which accommodates a layer 208 of a flexible foamed plastic material having a cut out 210 corresponding in shape to cut out 204. Formed over layer 208 and joined to substrate 202 and enclosing layer 208 is a forward layer 212, preferably formed of a semi rigid plastic material.

Forward head portion cover assembly 200 is formed with mutually spaced mutually facing edges 214 and 216 which, when the forward head portion cover assembly 200 is mounted onto head surrounding portion 114 of substrate 112 and over flexible cover 150, butt against corresponding edges facing edges 194 and 196 of top portion 190 of back cover assembly 170.

Battery pack 122 is illustrated in FIGS. 4A-4E and preferably includes a battery pack housing 220 and a removable battery 222 and may be entirely conventional.

Control unit 120 is illustrated in FIGS. 6A-6D and preferably includes a housing formed of a main housing portion 230 and a housing cover portion 232, which enclose a printed circuit board (PCB) 234. PCB 234 has a power connector 236 which is used to connect PCB 234 to battery pack 122 and is preferably provided with LED indicator lights 238, which are visible through correspondingly located apertures 240 formed in housing cover portion 232. LED indicator lights 238 indicate the energization state of electromagnetic field generating coil 130.

Also preferably mounted on the printed circuit board 234 are a system ON/OFF button 242 and a Bluetooth communication ON/OFF button 244, which are visible through correspondingly located apertures 246 and 248 formed in housing cover portion 232.

Control unit 120 communicates, preferably via Bluetooth, with a computerized communication device 250, such as a tablet or a smartphone, typically associated with a user. Preferably, the computerized communication device 250 is a computerized communication device 250 that has an app installed thereon, as described further below.

It is appreciated that, while in the illustrated embodiments of FIGS. 9A-10B computerized communication device 250 is shown being held by the user of body wearable treatment apparatus 100, computerized communication device 250 may be held by someone other than the user of body wearable treatment apparatus 100 and associated with body wearable treatment apparatus 100. Additionally, as described further hereinbelow, body wearable treatment apparatus 100 may also be operated remotely, for example by a provider, such as a doctor or a therapist.

Control unit 120 preferably provides the following principal functions:

Communication functionality 251, preferably via computerized communication device 250, such as a cellphone or a tablet as shown in FIGS. 9A-10B, with an external server 252 (FIG. 13) which may be cloud based, which stores treatment protocols, so as to download specific treatment protocols for a given patient at a given time. This communication is preferably wireless and external server 252 may be resident on the cloud. Preferably, external server 252 communicates with one or more databases 253 (FIG. 13), which may also be cloud based, in which are stored, inter alia, treatment protocols. The treatment protocols may implement one or more suitable electromagnetic field treatments, as taught, inter alia, in the above-referenced patent documents of the assignee, the contents of which are hereby incorporated by reference. Alternatively, control unit 120 may include a communication port, such as a Wi-Fi or a cellular port, through which communication functionality 251 communicates directly with external server 252.

Wave generation functionality 254, operative to control application of current by the electromagnetic field generating coil 130 in accordance with the downloaded specific treatment protocols for a given patient at a given time. Wave generation functionality 254 preferably generates a waveform from one or more waves, preferably selected from the group of sine wave, triangle wave and square wave, in a frequency range from 0 to 200 Hz. Alternatively, the wave form may be an arbitrary waveform, such as a combination of frequencies. Wave generation functionality 254 preferably generates an alternating magnetic field up to 500 Gauss RMS. More preferably, the Wave generation functionality 254 generates an alternating magnetic field of 10 Gauss RMS.

Feedback functionality 255 operative to provide feedback, such as confirming the progress of the specific treatment protocols.

It is appreciated that preferably, the user and a provider, such as a physician or a therapist, provide input, preferably via computerized communication device 250, preferably via the app installed thereon, to external server 252, which determines an initial specific treatment protocol for the specific patient, based, at least partially, on the input provided. Preferably, the patient is then able to continue the treatment protocol by utilizing the body wearable treatment apparatus 100 together with the app, either with or without the assistance of the provider. Alternatively, the input may be provided via a computerized communication device 275 (FIG. 13), such as a tablet or a smartphone, typically associated with a service provider, such as a physician, a hospital or a clinic. Preferably, the computerized communication device 275 is a computerized communication device 275 that has an app installed thereon, as described further below.

Figures 8A, 8B:
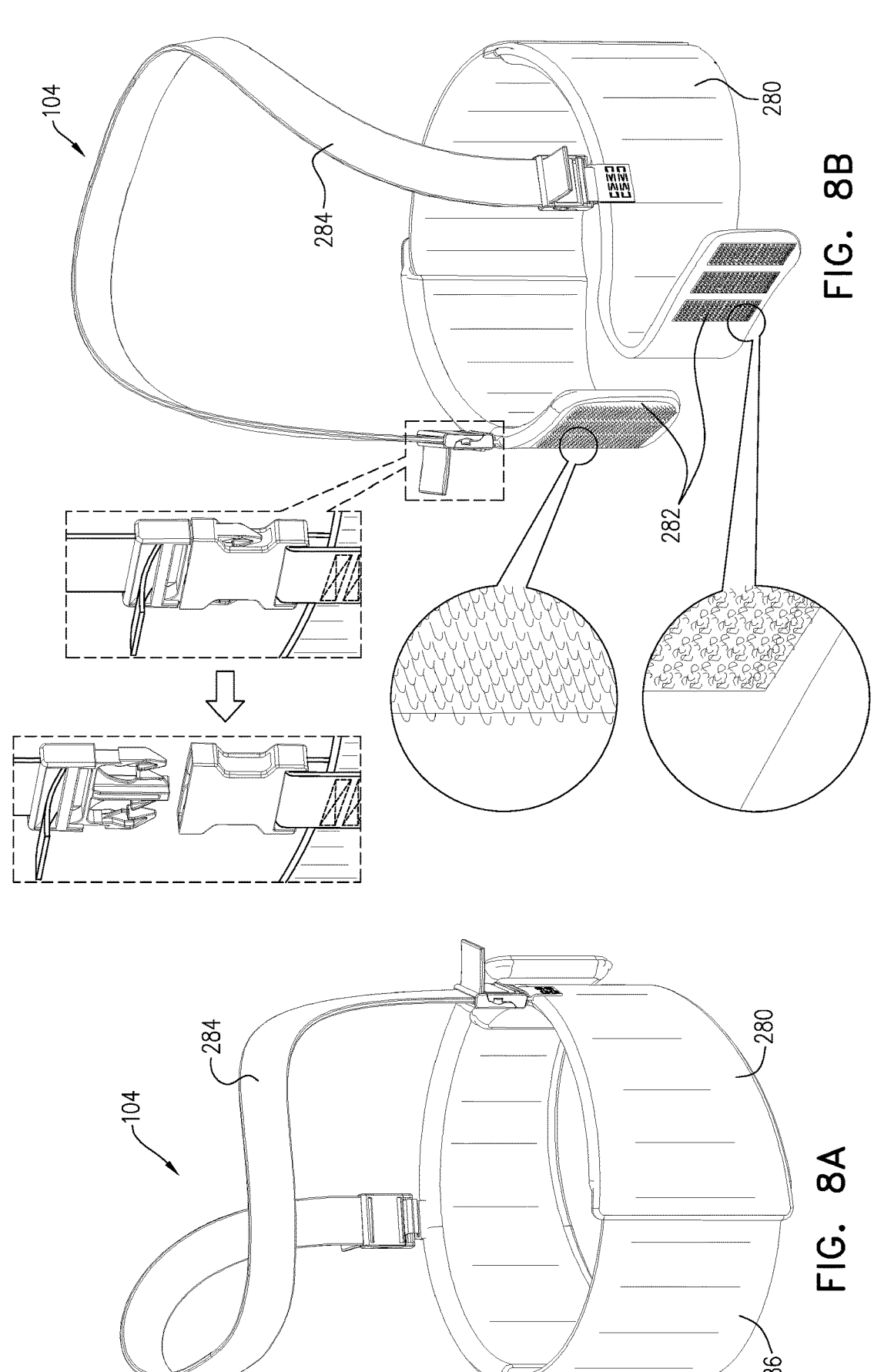
FIGS. 8A and 8B are simplified pictorial view illustrations of a support assembly forming part of the apparatus of FIGS. 1A-2B in respective closed and open operative orientations.

Referring now particularly to FIGS. 8A and 8B, it is seen that body mounting portion 104 preferably comprises a flexible band 280 formed with a VELCRO® type closure 282 and an adjustably mounted shoulder strap 284. Preferably, the flexible band 280 is formed at a rear portion thereof with a narrowed portion 286 which extends through channel 160 of coil mounting portion 102. Preferably, the dimensions of narrowed portion 286 and of channel 160 are such as to provide selectable vertical positioning of the coil mounting portion 102 onto the body mounting portion 104. It is appreciated that the pressure exerted by flexible band 280, when closed on a patient's body, and the action of shoulder strap 284 when snugly mounted onto the patient and engaging mounting channel 162 of coil mounting portion 102, retain the coil mounting portion 102 in a desired vertical position relative to body mounting portion 104.

Adjustment of the tightness of shoulder strap 284 is effective for positioning the upper part of coil mounting portion 102 with respect to the back and head of the patient. This can clearly be seen by comparing FIGS. 11A & 11B, which show a relatively loose orientation of the shoulder strap 284, with FIGS. 12A & 12B, which show a relatively tight orientation of the shoulder strap 284, bringing the upper part of the coil mounting portion 102 and the head surrounding portion 114 forward with respect to the patient. As seem particularly in FIG. 12B, the tightening of shoulder strap 284 preferably positions head surrounding portion 114 such that the head of the patient is in the center of head surrounding portion 114 and thereby in the center of the electromagnetic field induced by electromagnetic field generating coil 130.

It is appreciated that the provision of flexible band 280 of body mounting portion 104, together with the flexible coil support substrate 112, provide a custom comfortable fit of the body wearable treatment apparatus 100 to the body, and more specifically to the spinal contour, of the patient using the body wearable treatment apparatus 100.

In an alternative embodiment body mounting portion 104 may be in the form of a vest.

Figure 13:
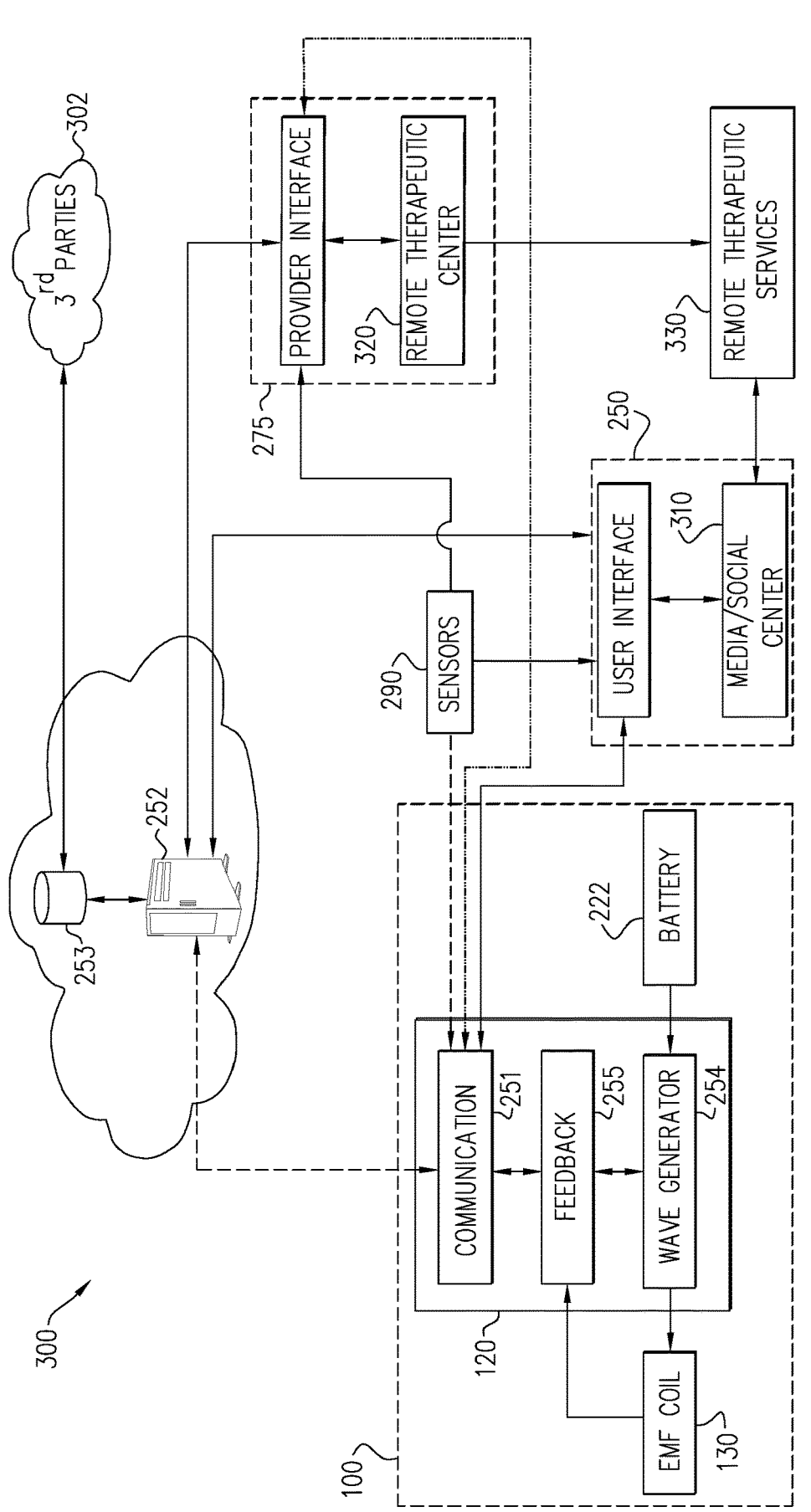
FIG. 13 is a simplified block diagram illustration of a system for treatment of neurological disorders of the central nervous system by application of electromagnetic fields, which is suitable for use with the apparatus of FIGS. 1-8B.

Reference is now additionally made to FIG. 13, which is a simplified block diagram illustration of a system 300 for treatment of neurological disorders of the central nervous system by application of electromagnetic fields, which is suitable for use with the body wearable treatment apparatus 100 of FIGS. 1-8B.

As seen in FIG. 13, system 300 preferably includes external server 252, which preferably communicates with one or more databases 253, which provide storage for information relating to treatment protocols and information relating to patients being treated using the treatment protocols. As seen further in FIG. 13, database 253 may receive additional information relating to treatments, such as success rate information, from other sources, such as other treatment providers 302, and may also provide aggregate data to other sources.

As seen in FIG. 13 and as described hereinabove, electronic control unit 120 of body wearable treatment apparatus 100 communicates, preferably through an app installed on computerized communication device 250, with external server 252 which provides treatment protocols, preferably as a waveform including a list of frequencies, intensities and durations in accordance with a formula describing an integral of frequencies, intensities and duration of a vector describing the waveform to be generated. Control unit 120 preferably includes a waveform generator which generates a current between −10 A to 10 A in the waveform provided by the external server 252, which is a protocol which is unique for the individual being treated using body wearable treatment apparatus 100. Alternatively, as described above, electronic control unit 120 may be operative to communicate directly with external server 252.

Computerized communication device 250 preferably provides the following functionalities, preferably through the app installed thereon:

Treatment feedback receiving functionality operative to receive feedback, such as real time sensed patient parameters provided by various sensors. These sensors may include, but are not limited to, EEG and EMG sensors 290, which may be mounted, as seen in FIGS. 9B and 10A, onto a helmet 292 and/or a glove 294, worn by the patient prior to, and/or during and/or following treatment. It is appreciated that, while in the illustrated embodiments of FIGS. 9B and 10A, sensors 290 are mounted onto helmet 292 and glove 294, sensors 290 may also be mounted directly onto the patient's skin. Alternatively, in an embodiment where electronic control unit 120 of body wearable treatment apparatus 100 communicates directly with external server 252, real time sensed patient parameters provided by sensors, such as sensors 290, may be received by electronic control unit 120 for transmission, by feedback functionality 255, to server 252.

Communication functionality providing communication between control unit 120 of body wearable treatment apparatus 100 and external server 252, which may be cloud based. The computerized communication device 250, such as a tablet or a smartphone, is used to identify the specific patient and identify the specific body wearable treatment apparatus 100 to match them for the given treatment session. The computerized communication device 250 receives the treatment protocol relevant to the specific patient from external server 252 and transmits the treatment protocol to control unit 120 for execution. The computerized communication device 250 receives the operational information relating to the treatment delivery, from control unit 120, and transmits the operational information together with as well the feedback, such as from sensors 290, to external server 252, which records the information for the specific patient for further retrieval. External server 252 also uses the operational information provided to validate the operation of body wearable treatment apparatus 100.

External server 252 preferably performs the following validation checks prior to transmitting the information relating to the current treatment session: a battery power check to ensure that battery 222 has sufficient power to complete the current treatment session and an identification of the specific body wearable treatment apparatus 100 being used and the user/patient to whom it is currently assigned to ensure that the proper treatment session parameters are transmitted to control unit 120 for application to the user/patient. Additionally, external server 252 preferably receives feedback from control unit 120 during the treatment session to ensure that the correct treatment session parameters are being applied by control unit 120.

Remote participation functionality, preferably through the app installed thereon and a similar app installed on a communication device, such as a tablet or a smartphone, of a provider, such as a physician or a therapist, which allows the provider to remotely participate in the treatment session and to monitor patient activity and progress.

System upgrade functionality, which ensures that the body wearable treatment apparatus 100 is utilizing the most current treatment protocol information.

Additional therapy functionality, which provides the patient a series of additional therapies other than the EMF treatment, such as physiotherapy, occupational therapy, and/or games and tasks to enhance the effect of the treatment, and thereby the recovery of the patient, as well as providing entertainment for the patient during the EMF treatment.

Patient feedback functionality, which provides the patient with feedback regarding their progress, such as from external server 252 or from their provider.

Social community functionality which allows the patient to participate in a social community. The social community may provide the patient with access to people with similar conditions, for discussions of their condition and/or treatment and/or other social interactions. Additionally, the patient may be able to contact doctors and other health professionals for assistance/guidance. The social community may also provide information updates regarding the patient's specific condition as well as general emotional and social support.

It is appreciated that some or all of the above functionalities may be provided in conjunction with a media/social center app 310 installed on computerized communication device 250.

Additionally, it is noted that the app installed on computerized communication device 250 may communicate with one or more body wearable treatment apparatus 100 concurrently and may also be operative to provide patient data, such as in the form of a patient tracking log and analytics relating to the patient and/or the treatment, relating to each of the body wearable treatment apparatuses 100. For example, multiple users/patients in the same location, each associated with a different body wearable treatment apparatus 100, may utilize the same computerized communication device 250.

Additionally or alternatively, system 300 may include at least one computerized communication device 275, such as a tablet or a smartphone, associated with a service provider, such as a physician, a hospital or a clinic. Preferably, the computerized communication device 275 is a computerized communication device 275 that has an app installed thereon, the functions of which are described further below.

It is appreciated that the some or all of the functionality described hereinabove with reference to computerized communication device 250 may also be included in an app installed on computerized communication device 275.

Computerized communication device 275 preferably additionally provides the following functionalities, preferably through the app installed thereon:

Multiple device functionality for operation of and data gathering from one or more body wearable treatment apparatus 100 concurrently. Computerized communication device 275 may also access relevant clinical data relating to a different users/patients undergoing treatment to assist in patient management by the provider, such as a physician or a therapist, by providing patient data, such as in the form of a patient tracking log and analytics relating to the patient and/or the treatment. Additionally, the app installed on computerized communication device 275 preferably provides treatment update functionality operative to monitor patient progress and refine the treatment needed for the specific patient. The app installed on computerized communication device 275 preferably allows the provider to modify the treatment based on, inter alia, external information, patient progress and electro-neurological examination.

It is further noted that the app installed on computerized communication device 250 or the app installed on computerized communication device 275 may also provide patient management functionality in the form of, inter alia, following up the patient drug administration, treatment sessions, and the use of the body wearable treatment apparatus 100 and providing this data to server 252. Server 252 will preferably maintain the patient activity information and provide a record of treatments and progress.

Server 252 will also preferably provide patient information to the provider via the app installed on computerized communication device 275 for later analysis which will enable the medical and treatment team to evaluate the patient activity and progress. Additionally, the app installed on computerized communication device 275 preferably includes data retrieval and analysis functionality operative to retrieve stored information from server 252 and other sources and generate statistical analysis of a patient, as well as population statistics. The app installed on computerized communication device 275 may also include remote therapeutic provision functionality 320 operative to provide patients with access to external remote therapeutic services 330.

It is appreciated that the communication between electronic control unit 120 and server 252 enables the patient to receive treatments, using body wearable treatment apparatus 100, during the process of recovery in different places, such as in a hospital, a clinic, a care center, a rehabilitation facility, their own home or any other suitable location, in a comfortable and suitable position. Additionally, body wearable treatment apparatus 100 enables the patient to participate in other activities, such as physiotherapy, occupational therapy and cognitive training, during the EMF treatment.

The body wearable treatment apparatus 100 preferably generates therapeutically beneficial electromagnetic fields in the vicinity thereof for treatment of neurological disorders of the central nervous system as described, inter alia, in assignee's patent documents referenced above, the teachings of which are hereby incorporated by reference herein.

In accordance with an embodiment of the present invention, the body wearable treatment apparatus 100 of FIGS. 1-8B may be employed as part of a system for treatment of neurological disorders of the central nervous system, such as that described hereinbelow with reference to FIG. 13, including a database indicating electromagnetic frequencies associated with specific motor functions in a sample of healthy persons; an initial treatment protocol generator receiving information identifying impaired motor functions of a given patient and employing said database to generate an initial treatment protocol which is not based on an electroneurological examination of the patient and an electromagnetic field generator operative to applying electromagnetic energy to the patient in accordance with the initial treatment protocol, prior to electroneurological examination of the patient.

Alternatively or additionally, the body wearable treatment apparatus of FIGS. 1-8B may be employed with any other suitable system for treatment of neurological disorders of the central nervous system, including, without limitation, those described in assignee's patent documents referenced above, the teachings of which are hereby incorporated by reference herein.

Alternatively or additionally, the system described hereinbelow with reference to FIG. 13 may be employed with any suitable apparatus other than that described hereinabove with reference to FIGS. 1-8B and the body wearable treatment apparatus 100 of FIGS. 1-8B may be employed with any other suitable system for treatment of neurological disorders of the central nervous system, including, without limitation, those described in assignee's patent documents referenced above, the teachings of which are hereby incorporated by reference herein.

It is appreciated that body wearable treatment apparatus 100 and server 252, together with databases 253, enable an initial treatment protocol to be established based on identified impaired motor functionality and/or other functionality of a patient without waiting for an electroneurological examination of the patient. It is further appreciated that the treatment protocol may be varied over time based on, inter alia, external data, patient progress and/or electroneurological examination of the patient.

It will be appreciated by persons skilled in the art that the present invention is not limited by what has been particularly shown and described hereinabove. Rather the scope of the invention includes combinations and subcombinations of the various novel features described hereinabove as well as equivalents thereof, which are not in the prior art.

The invention claimed is:

1. Body wearable treatment apparatus for treatment of neurological disorders and conditions of a central nervous system by application of electromagnetic fields thereto, the apparatus comprising:

a coil mounting portion comprising a head surrounding portion positionable with respect to a head of a patient and extending to a back portion positionable with respect to a back of the patient, and including an electromagnetic field generating coil extending from the head surrounding portion down along a length of the back portion; and a body mounting portion, said coil mounting portion being removably mounted on said body mounting portion.

2. Body wearable treatment apparatus for treatment of neurological disorders and conditions of the central nervous system by application of electromagnetic fields thereto according to claim 1 and wherein said coil mounting portion is selectably positionable relative to said body mounting portion.

3. Body wearable treatment apparatus for treatment of neurological disorders and conditions of the central nervous system by application of electromagnetic fields thereto according to claim 1 and also comprising an electronic control unit.

4. Body wearable treatment apparatus for treatment of neurological disorders and conditions of the central nervous system by application of electromagnetic fields thereto according to claim 3 and wherein said control unit provides at least one of the following functions:

communication with an external server which stores treatment protocols so as to download specific treatment protocols for a given patient at a given time;

wave generation functionality operative to control application of current to said electromagnetic field generating coil in accordance with said specific treatment protocols for said given patient at said given time; and feedback functionality operative to provide feedback confirming progress of said specific treatment protocols.

5. Body wearable treatment apparatus for treatment of neurological disorders and conditions of the central nervous system by application of electromagnetic fields thereto according to claim 3 and wherein said control unit provides at least two of the following functions:

communication with an external server which stores treatment protocols so as to download specific treatment protocols for a given patient at a given time;

wave generation functionality operative to control application of current to said electromagnetic field generating coil in accordance with said specific treatment protocols for said given patient at said given time; and feedback functionality operative to provide feedback confirming progress of said specific treatment protocols.

6. Body wearable treatment apparatus for treatment of neurological disorders and conditions of the central nervous system by application of electromagnetic fields thereto according to claim 3 and wherein said control unit provides all of the following functions:

communication with an external server which stores treatment protocols so as to download specific treatment protocols for a given patient at a given time;

wave generation functionality operative to control application of current to said electromagnetic field generating coil in accordance with said specific treatment protocols for said given patient at said given time; and feedback functionality operative to provide feedback confirming progress of said specific treatment protocols.

7. Body wearable treatment apparatus for treatment of neurological disorders and conditions of the central nervous system by application of electromagnetic fields thereto according to claim 1 and wherein said coil mounting portion comprises:

a coil support substrate, formed to define the head surrounding portion and the back portion; and the electromagnetic field generating coil mounted onto said coil support substrate.

8. Body wearable treatment apparatus for treatment of neurological disorders and conditions of the central nervous system by application of electromagnetic fields thereto according to claim 7 and wherein said electromagnetic field generating coil is a single coil, which is connected to an electronic control unit at opposite ends thereof.

9. Body wearable treatment apparatus for treatment of neurological disorders and conditions of the central nervous system by application of electromagnetic fields thereto according to claim 7 and wherein said electromagnetic field generating coil is formed of a flat braided conductor.

10. Body wearable treatment apparatus for treatment of neurological disorders and conditions of the central nervous system by application of electromagnetic fields thereto according to claim 7 and wherein said electromagnetic field generating coil is arranged in interconnected upper and lower electromagnetic field generating coil winding portions.

11. Body wearable treatment apparatus for treatment of neurological disorders and conditions of the central nervous system by application of electromagnetic fields thereto according to claim 10 and wherein said upper electromagnetic field generating coil winding portion extends along said coil support substrate adjacent a top edge of said head surrounding portion and up and down along said length of said back portion at an interior thereof.

12. Body wearable treatment apparatus for treatment of neurological disorders and conditions of the central nervous system by application of electromagnetic fields thereto according to claim 10 and wherein said lower electromagnetic field generating coil winding portion extends along said coil support substrate adjacent a bottom edge of said head surrounding portion thereof and up and down along a length of said back portion adjacent an edge thereof.

13. Body wearable treatment apparatus for treatment of neurological disorders and conditions of the central nervous system by application of electromagnetic fields thereto according to claim 7 and wherein said electromagnetic field generating coil comprises multiple coil windings, which are retained in a mutually stacked orientation by connectors.

14. Body wearable treatment apparatus for treatment of neurological disorders and conditions of the central nervous system by application of electromagnetic fields thereto according to claim 1 and wherein said body mounting portion comprises a flexible band with a narrowed portion formed at a rear portion thereof.

15. Body wearable treatment apparatus for treatment of neurological disorders and conditions of the central nervous system by application of electromagnetic fields thereto according to claim 14 and wherein said coil mounting portion comprises a channel through which said flexible band extends, thereby providing selectable vertical positioning of said coil mounting portion onto said body mounting portion.

16. Body wearable treatment apparatus for treatment of neurological disorders and conditions of the central nervous system by application of electromagnetic fields thereto according to claim 1 and wherein said body mounting portion comprises a shoulder strap.

17. Body wearable treatment apparatus for treatment of neurological disorders and conditions of the central nervous system by application of electromagnetic fields thereto according to claim 16 and wherein said shoulder strap is configured to position said coil mounting portion relative to the patient.

18. A system for treatment of neurological disorders and conditions of a central nervous system by application of electromagnetic fields thereto, the system comprising:

at least one database storing information relating to treatment protocols;

a server communicating with said at least one database; and a body wearable treatment apparatus communicating with said server, said body wearable treatment apparatus comprising:

a coil mounting portion comprising a head surrounding portion positionable with respect to a head of a patient and extending to a back portion positionable with respect to a back of the patient, and including an electromagnetic field generating coil extending from the head surrounding portion down along a length of the back portion; and a body mounting portion, said coil mounting portion being removably mounted on said body mounting portion.

19. A system for treatment of neurological disorders and conditions of the central nervous system by application of electromagnetic fields thereto according to claim 18 and also comprising sensors for sensing real time sensed patient parameters.

20. A system for treatment of neurological disorders and conditions of the central nervous system by application of electromagnetic fields thereto according to claim 19 and wherein said sensors are mounted on removably wearable substrates.

21. A system for treatment of neurological disorders and conditions of the central nervous system by application of electromagnetic fields thereto according to claim 20 and wherein said removably wearable substrates are selected from a helmet and a glove.

\*    \*    \*    \*    \*